United States Patent
Okamoto

(10) Patent No.: US 10,517,463 B2
(45) Date of Patent: Dec. 31, 2019

(54) ENDOSCOPE OPERATION MECHANISM AND ENDOSCOPE

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 278 days.

(21) Appl. No.: 15/447,551

(22) Filed: Mar. 2, 2017

(65) Prior Publication Data

US 2017/0172386 A1   Jun. 22, 2017

Related U.S. Application Data

(63) Continuation of application No. PCT/JP2015/074961, filed on Sep. 2, 2015.

(30) Foreign Application Priority Data

Jan. 9, 2015   (JP) .................................. 2015-003267

(51) Int. Cl.
*A61B 1/00* (2006.01)
*A61B 1/005* (2006.01)
*G02B 23/24* (2006.01)

(52) U.S. Cl.
CPC .......... *A61B 1/00071* (2013.01); *A61B 1/005* (2013.01); *A61B 1/00045* (2013.01);
(Continued)

(58) Field of Classification Search
CPC ... A61B 1/00066; A61B 1/005; A61B 1/0051; A61B 1/0052; A61B 1/0057; G02B 23/24; G02B 23/2476
(Continued)

(56) References Cited

U.S. PATENT DOCUMENTS 5,007,406 A  *  4/1991  Takahashi ............ A61B 1/0052
                                                               600/119
5,014,685 A       5/1991  Takahashi
                   (Continued)

FOREIGN PATENT DOCUMENTS

EP       2821000 A1    1/2015
JP    H06-054795 A     3/1994
           (Continued)

OTHER PUBLICATIONS

International Search Report dated Nov. 17, 2015 issued in PCT/JP2015/074961.
(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope operation mechanism includes: a dial operating an endoscope function; a detection sensor that has a sensor rotation shaft to which rotation of a dial rotation shaft of the dial is transmitted and detects the rotation amount, and that outputs an electrical signal in accordance with the detected rotation amount to a control portion performing driving control of a driving source of the endoscope function; an initial position reversion mechanism applying a rotational force to the dial rotation shaft in an opposite direction to the direction in which the dial rotation shaft is rotated, to thereby cause the rotational position of the dial to return to an initial position; and a switching mechanism switchable between a first state in which a rotational force from the initial position reversion mechanism is applied to the dial rotation shaft, and a second state in which the rotational force is not applied.

17 Claims, 32 Drawing Sheets

(52) U.S. Cl.
CPC ........ *A61B 1/0052* (2013.01); *A61B 1/00066* (2013.01); *G02B 23/2476* (2013.01)

(58) Field of Classification Search
USPC ........................................ 600/146, 147, 150
See application file for complete search history.

(56) References Cited

U.S. PATENT DOCUMENTS

| | | | | |
|---|---|---|---|---|
| 5,488,946 | A * | 2/1996 | Calhoun ................. | A62B 7/02 128/205.21 |
| 5,658,238 | A | 8/1997 | Suzuki et al. | |
| 8,317,686 | B2 * | 11/2012 | Ashida ................. | A61B 1/0052 600/145 |
| 2004/0054258 | A1 * | 3/2004 | Maeda ............... | A61B 1/00039 600/152 |
| 2009/0227841 | A1 * | 9/2009 | Miyako .............. | A61B 1/00039 600/139 |
| 2011/0065994 | A1 * | 3/2011 | Kudoh ................. | A61B 1/0051 600/146 |
| 2011/0319921 | A1 * | 12/2011 | Giotis .............. | A61B 17/32053 606/187 |
| 2012/0302832 | A1 | 11/2012 | Inada | |
| 2013/0158379 | A1 * | 6/2013 | Selkee ................. | A61B 1/0052 600/373 |
| 2014/0135580 | A1 | 5/2014 | Omoto et al. | |
| 2014/0371534 | A1 * | 12/2014 | Okamoto ........... | A61B 1/00066 600/118 |
| 2015/0054445 | A1 * | 2/2015 | Kawai ................ | A61B 1/00006 318/630 |
| 2015/0208902 | A1 | 7/2015 | Okamoto | |

FOREIGN PATENT DOCUMENTS

| | | |
|---|---|---|
| JP | 2010-214043 A | 9/2010 |
| JP | 2014-161644 A | 9/2014 |
| WO | WO 2013/129494 A1 | 9/2013 |
| WO | 2014/203673 A1 | 12/2014 |

OTHER PUBLICATIONS

Extended Supplementary European Search Report dated Apr. 6, 2018 in European Patent Application No. 15 87 6915.8.

* cited by examiner

ENDOSCOPE OPERATION MECHANISM AND ENDOSCOPE

CROSS REFERENCE TO RELATED APPLICATION

This application is a continuation application of PCT/JP2015/074961 filed on Sep. 2, 2015 and claims benefit of Japanese Application No. 2015-003267 filed in Japan on Jan. 9, 2015, the entire contents of which are incorporated herein by this reference.

BACKGROUND OF THE INVENTION

1. Field of the Invention

The present invention relates to an endoscope operation mechanism equipped with a bending operation portion for performing an operation to bend a bending portion provided in an insertion portion of an endoscope, and an endoscope.

2. Description of the Related Art

In order to perform, for example, observation and treatment of a lesion inside a subject, an endoscope conventionally includes an insertion portion having flexibility that is inserted into the subject, and an operation apparatus that performs operations for bending the insertion portion in the UD (upward/downward) direction and the RL (right/left) direction.

In such an endoscope, the operation apparatus is provided with a UD angle knob configured to perform operations in the UD direction and an RL angle knob configured to perform operations in the RL direction.

When an operator of the endoscope performs observation and treatment of a lesion or the like, the operator operates the UD angle knob and the RL angle knob to cause a bending portion that is provided in the insertion portion to bend in the UD direction and RL direction.

For example, International Publication No. WO2013/129494 discloses technology that improves the bending operability in the UD direction and the RL direction of an insertion portion in such an endoscope.

In International Publication No. WO2013/129494, an endoscope as an insertion apparatus is disclosed in which a knob is provided configured to perform upward/downward (UD) bending operations of the insertion portion, and an RL operation dial is arranged configured to bend the insertion portion in the right/left (RL) direction.

In the conventional endoscope, a rotational state of an RL operation dial that instructs a bending operation of an insertion portion by rotating an operation element for right/left (RL) direction bending within an arbitrary rotational angle range from 0 to ±90 degrees can be maintained to thereby maintain a bending state of a bending portion.

Further, with respect to the conventional endoscope, technology has been disclosed regarding a reversion function that, when the RL operation dial is rotated by an amount greater than the arbitrary rotational angle that was set, causes the RL operation dial to return to a position within the rotational angle range that includes an initial position (a neutral position of the RL dial).

SUMMARY OF THE INVENTION

An endoscope operation mechanism according to one aspect of the present invention is arranged in an operation portion that is provided on a proximal end side of an insertion portion in an endoscope, the endoscope operation mechanism including: a first operation member that is constituted by a rotational operation member that is provided in a rotatable manner about a predetermined axis, and that is configured to actuate a function of the endoscope upon being operated by an operator and rotating from an initial state; an initial state reversion mechanism configured to apply an urging force to the first operation member so as to return the first operation member to the initial state; and a second operation member that is rotatably disposed on a shaft that is parallel to a rotation shaft of the first operation member, and that is configured to switch between a first state that allows a change in position of the first operation member under the urging force, and a second state that suppresses a change in position of the first operation member in resistance to the urging force, upon being rotationally operated by an operator.

DETAILED DESCRIPTION OF THE PREFERRED EMBODIMENT(S)

An endoscope that is the present invention is described hereunder. Note that, in the following description, drawings that are based on each embodiment are schematic ones in which a relationship between a thickness and a width of each portion, thickness ratios of the respective portions and the like are different from those of actual portions, and the drawings may include portions in which dimensional relationships and ratios are different from one another.

First Embodiment

Figure 1:
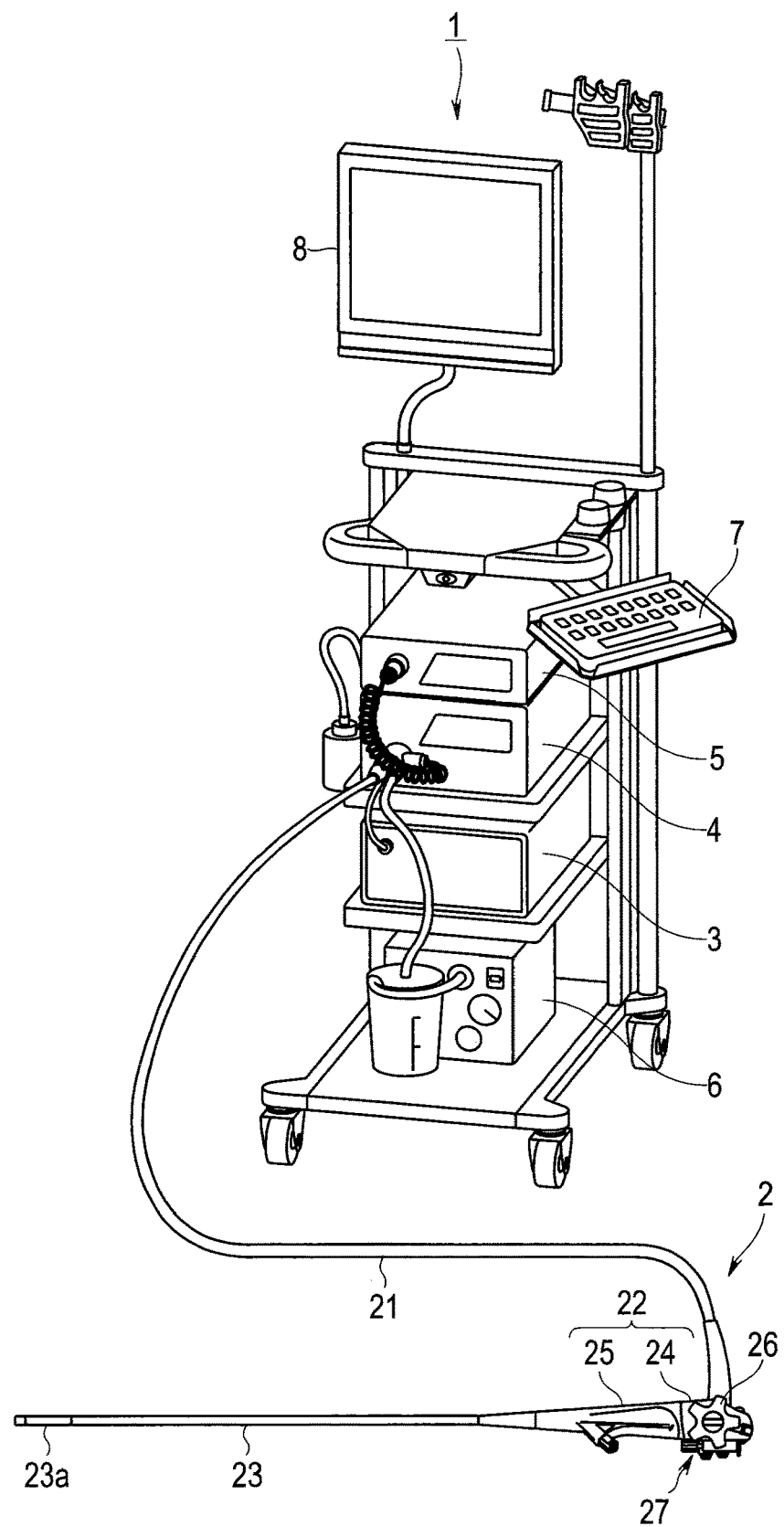
FIG. 1 is an overall configuration diagram illustrating an endoscope apparatus of a first embodiment according to the present invention.
Figure 2:
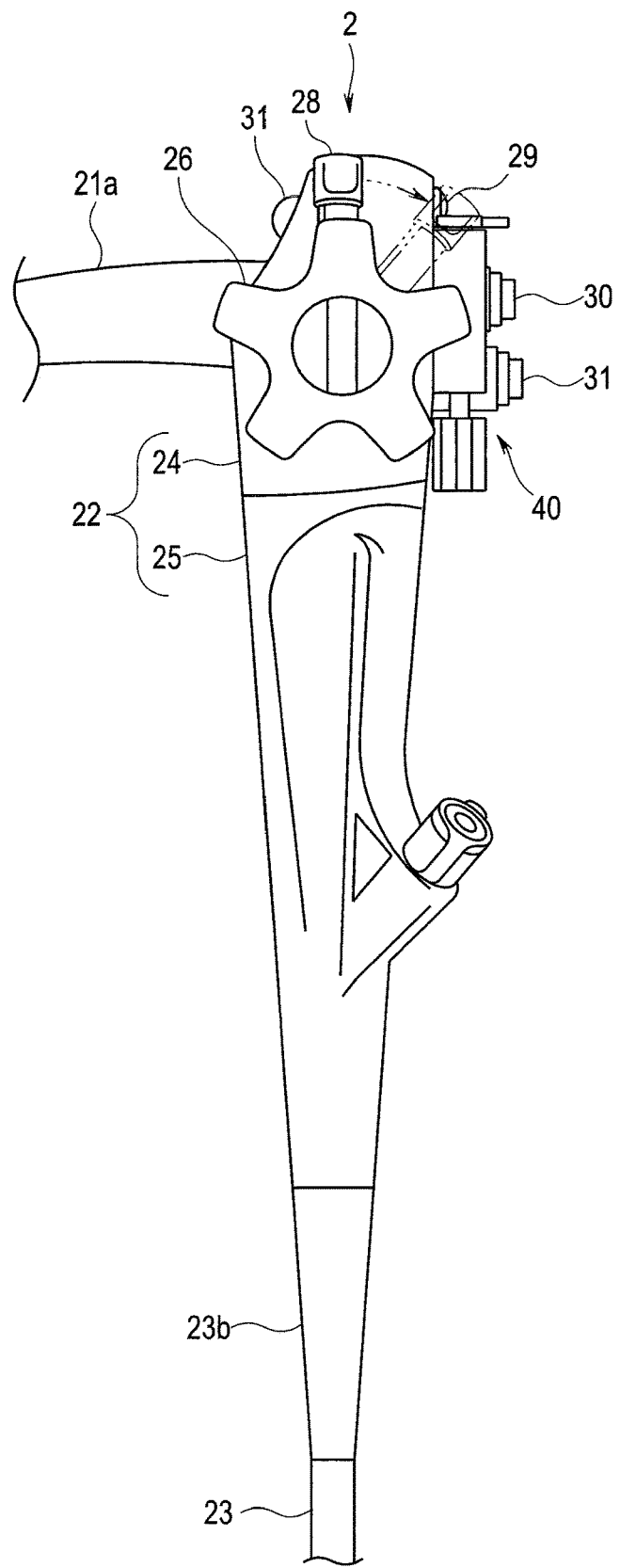
FIG. 2 is a side view illustrating the configuration of an operation portion of the first embodiment according to the present invention.
Figure 3:
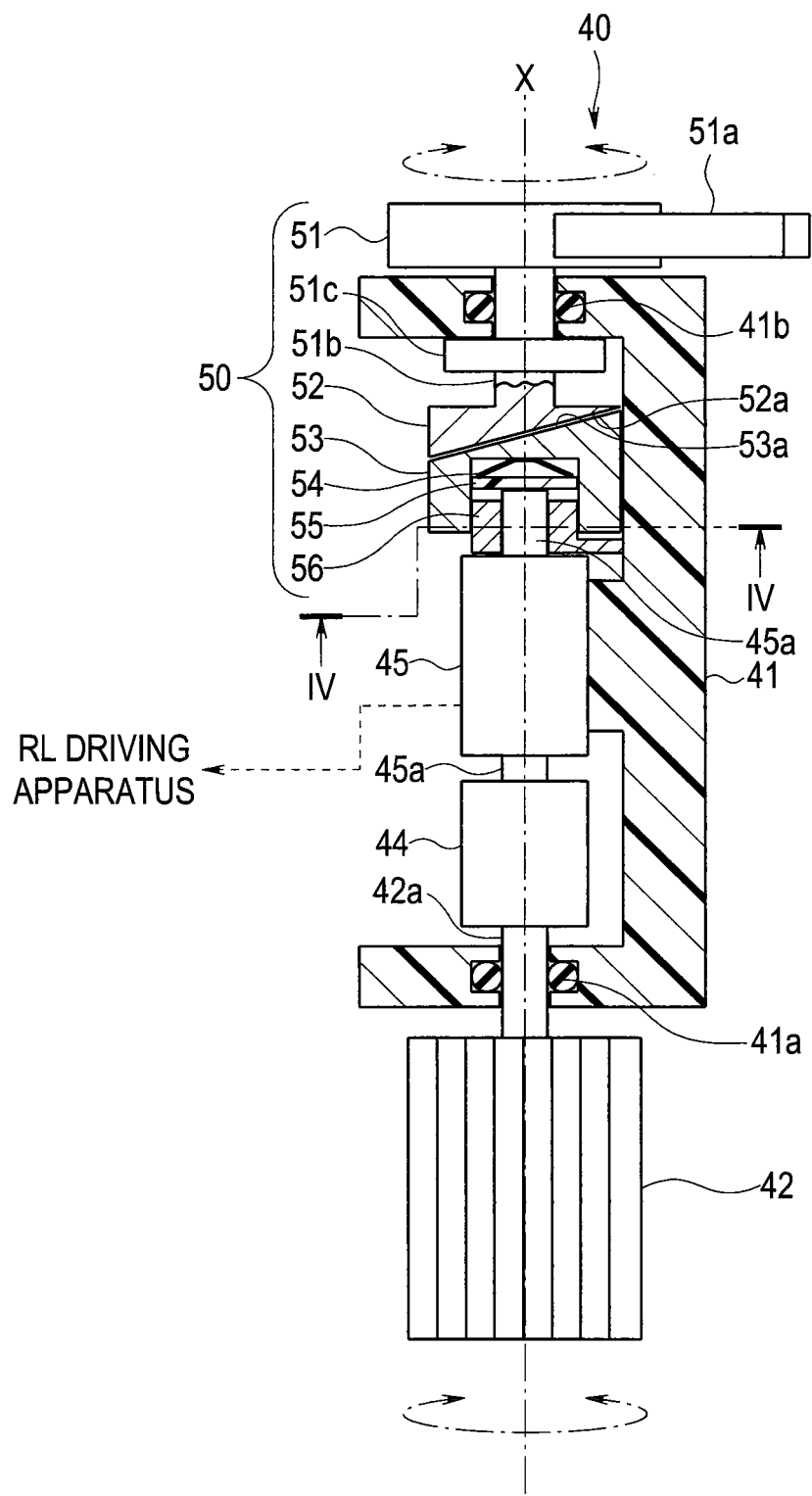
FIG. 3 is a cross-sectional view illustrating the configuration of an RL angular operation portion of the first embodiment according to the present invention.
Figure 4:
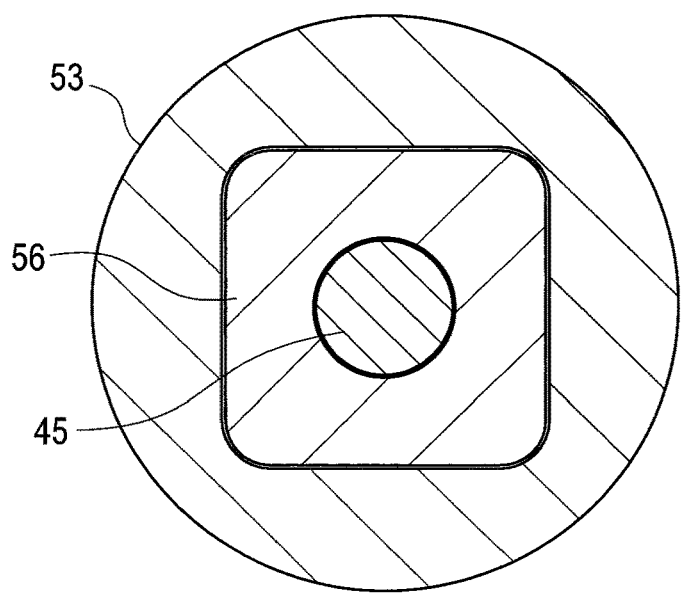
FIG. 4 is a cross-sectional view illustrating a second cam, a cam guide and a sensor rotation shaft that is taken along a line IV-IV in FIG. 3 of the first embodiment according to the present invention.
Figure 5:
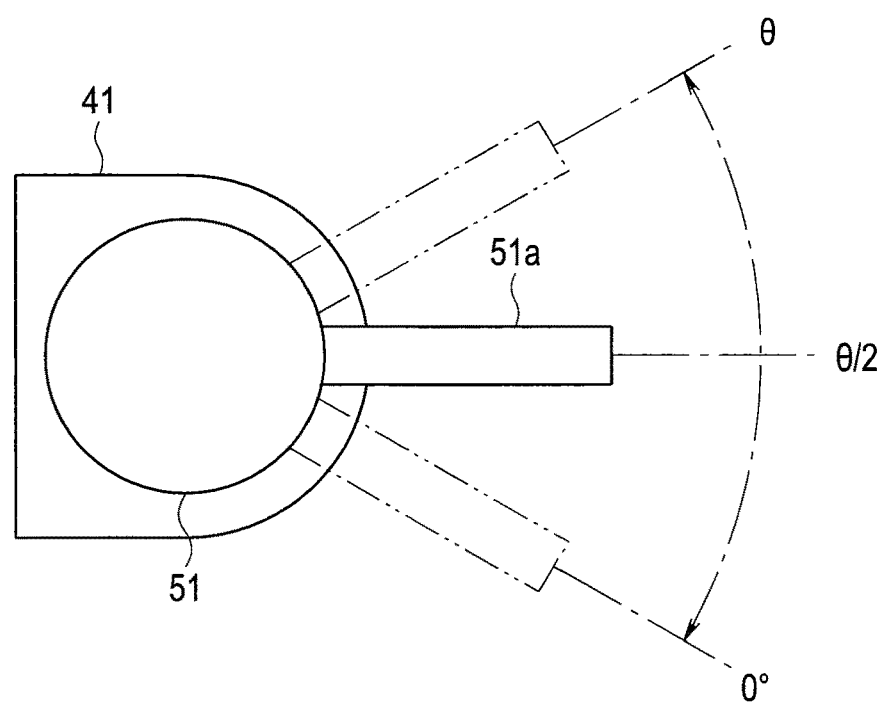
FIG. 5 is a plan view illustrating an operating range of an RL engagement lever of the first embodiment according to the present invention.
Figure 6:
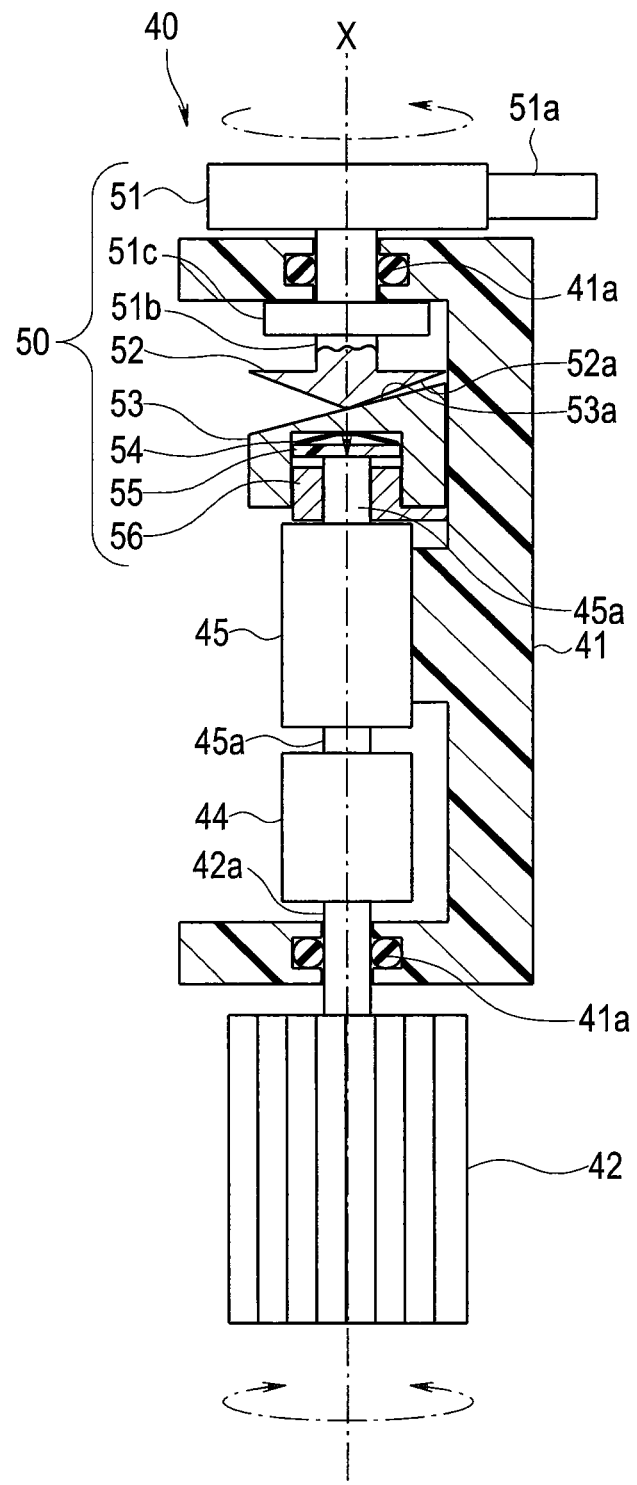
FIG. 6 is a cross-sectional view for describing an action of the RL angular operation portion of the first embodiment according to the present invention.
Figure 7:
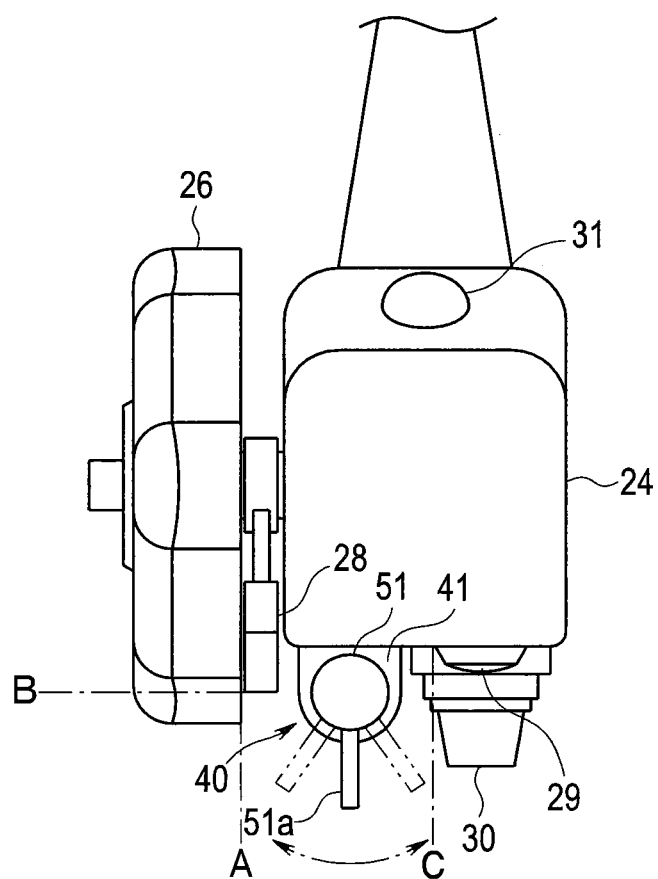
FIG. 7 is a front view of an operation portion for describing the operating range of the RL engagement lever of the first embodiment according to the present invention.
Figure 8:
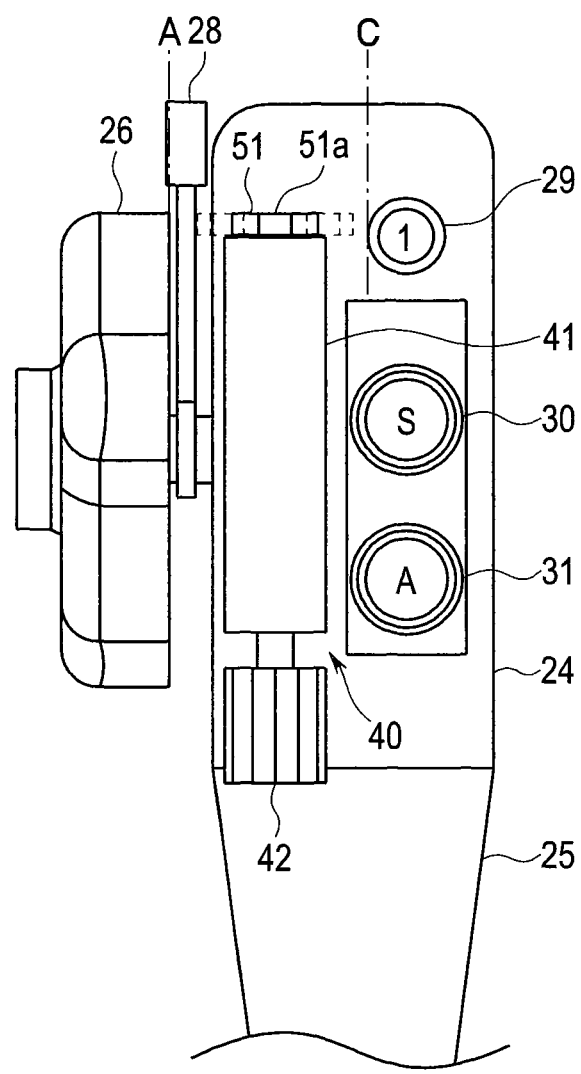
FIG. 8 is a top view of an operation portion for describing the operating range of the RL engagement lever of the first embodiment according to the present invention.
Figure 9:
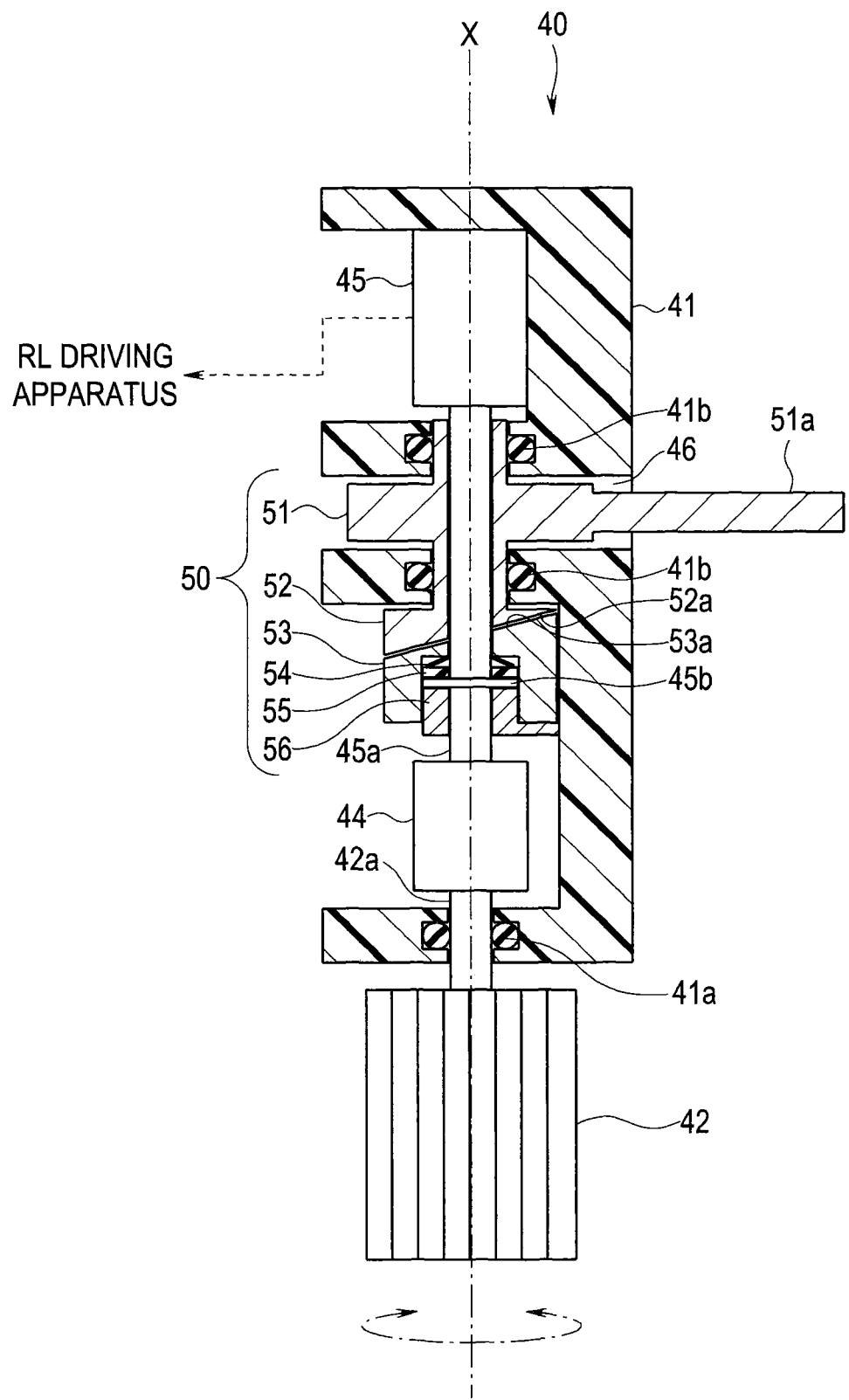
FIG. 9 is a cross-sectional view illustrating the configuration of an RL angular operation portion according to a modification of the first embodiment according to the present invention.
Figure 10:
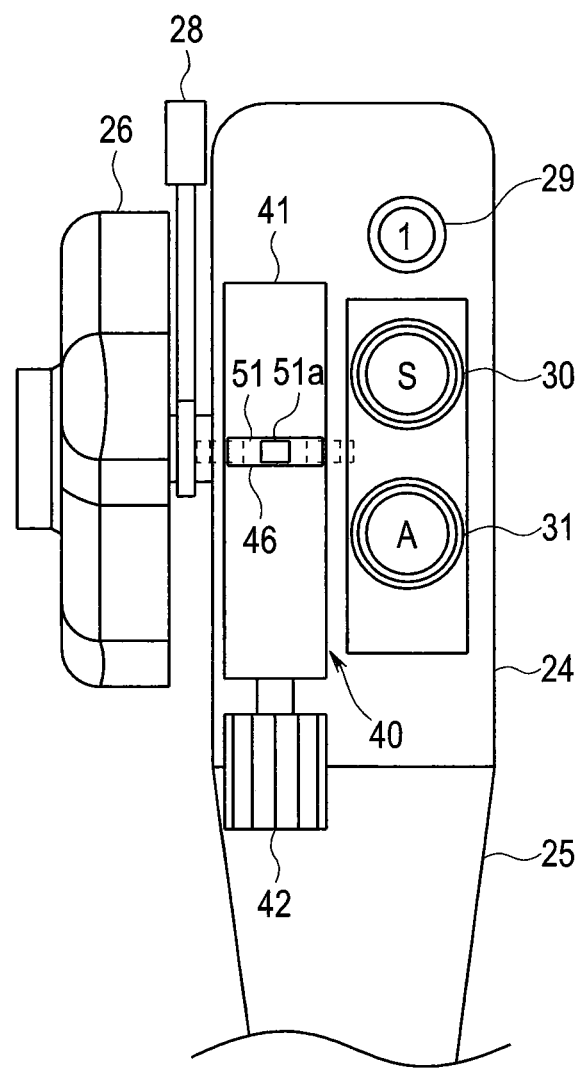
FIG. 10 is a front view of an operation portion for describing an operating range of an RL engagement lever of the modification of the first embodiment according to the present invention.

First, a first mode of the present invention will be described based on the accompanying drawings. FIG. 1 to FIG. 10 relate to a first embodiment of the present invention. FIG. 1 is an overall configuration diagram that illustrates an endoscope apparatus. FIG. 2 is a side view that illustrates the configuration of an operation portion. FIG. 3 is a cross-sectional view that illustrates the configuration of an RL angular operation portion. FIG. 4 is a cross-sectional view that illustrates a second cam, a cam guide and a sensor rotation shaft that is taken along a line IV-IV in FIG. 3. FIG. 5 is a plan view that illustrates an operating range of an RL engagement lever. FIG. 6 is a cross-sectional view for describing an action of an RL angular operation portion. FIG. 7 is a front view of an operation portion for describing an operating range of the RL engagement lever. FIG. 8 is a top view of the operation portion for describing the operating range of the RL engagement lever. FIG. 9 is a cross-sectional view that illustrates the configuration of an RL angular operation portion according to a modification. FIG. 10 is a front view of an operation portion for describing an operating range of an RL engagement lever according to the modification.

As illustrated in FIG. 1, an endoscope apparatus 1 includes an endoscope 2, a control apparatus 3, a light source apparatus 4, an image photographing apparatus 5, a water feeding apparatus 6, a keyboard 7 and a monitor 8. The control apparatus 3 controls lighting of the light source apparatus 4 and also controls feeding of water to the endoscope 2 by the water feeding apparatus 6, and controls so that an image of a subject that was photographed through the endoscope 2 undergoes image processing by the image photographing apparatus 5 and is displayed on the monitor 8.

The endoscope 2 is configured to include a universal cord 21, an operation portion 22 that is an operation apparatus, and an insertion portion 23. The endoscope 2 is connected through the universal cord 21 to the control apparatus 3, the light source apparatus 4, the image photographing apparatus 5 and the water feeding apparatus 6.

Upon being operated by an operator that is a surgeon, the operation portion 22 actuates the bending portion 23a of the insertion portion 23 in an upward/downward direction (UD direction) in an observation image as a first direction, and in a right/left direction (RL direction) in the observation image as a second direction which is different to, in this case, substantially orthogonal to, the first direction.

The insertion portion 23 is a portion that is inserted into a subject, and is formed of a flexible member. The bending portion 23a of the insertion portion 23 bends in the UD direction and the RL direction in an observation image when bending operation means provided in the operation portion 22 is operated.

As shown in FIG. 2, the operation portion 22 of the endoscope 2 is constituted by integrally connecting an operation portion main body 24 and a grip 25 that is a grasping portion. Note that, in a state in which an operator that is a user (surgeon) grasps the grip 25 of the operation portion 22 with one hand, the operation portion main body 24 is taken as the upper side and the grip 25 and the insertion portion 23 are taken as the lower side. To paraphrase the foregoing description in terms of the direction along which the insertion portion 23 extends, the operation portion main body 24 can be expressed as the proximal end side and the insertion portion 23 can be expressed as the distal end side.

The universal cord 21 shown in FIG. 1 is connected via a bend preventing portion 21a to the operation portion main body 24. The insertion portion 23 is connected in a continuous fashion to the grip 25.

The operation portion main body 24 and the grip 25 are formed in a shape such that the operation portion main body 24 and the grip 25 fit in the palm of one hand of the operator in a state in which the operator grasps mainly the grip 25 with the relevant one hand, for example, in a shape with the thickness gradually decreasing from the operation portion main body 24 toward the grip 25.

The grip 25 is a substantially conical shape and is formed so that the diameter of the grip 25 becomes gradually thinner from the lower end of the operation portion main body 24 in the direction of the insertion portion 23 to which the grip 25 is connected through a bend preventing portion 23b.

On one side face of the operation portion main body 24, a UD angle knob 26 that is a first angle mechanism as UD bending operation means configured to bend the bending portion 23a of the insertion portion 23 in the upward/downward direction (UD direction) in an observation image in accordance with a rotational operation that is manually performed by the operator, and a UD knob engagement lever 28 as a UD-side engagement portion configured to fix a rotational position of the UD angle knob 26 and to fix or release a bending angle in a UD bending direction of the bending portion 23a of the insertion portion 23 are provided.

In a state in which the operator grasps mainly the grip 25 in the palm of one hand, the UD angle knob 26 is rotationally operated by the operator using, for example, the thumb and the forefinger or, depending on the operator, the thumb and the middle finger or the like. Note that the UD knob engagement lever 28 is operated by, for example, the thumb of the hand with which the operator grasps the grip, or by the thumb and/or the forefinger of the hand, or by the thumb and/or the forefinger of a hand which the operator is not using to grasp the grip.

Note that, in this case, the UD knob engagement lever 28 can fix the bending angle of the bending portion 23a by being tilted to the right side as viewed from the front of the sheet in FIG. 2.

Further, on another side face that intersects with the one side face of the operation portion main body 24 on which the UD angle knob 26 is provided, an RL angular operation portion 40 is provided as an endoscope operation mechanism that is a second angle mechanism as RL bending operation means configured to bend the bending portion 23a of the insertion portion 23 in the right/left direction (RL direction) in an observation image.

The RL angular operation portion 40 as the endoscope operation mechanism is subjected to a predetermined operation by, for example, the forefinger, or depending on the operator, the middle finger or the like, in a state in which the operator mainly grasps the grip 25 in the palm of one hand. That is, the RL angular operation portion 40 is operated by a finger other than a thumb of the operator.

Note that an unshown RL driving apparatus that serves as a driving source is provided in the operation portion main body 24. The RL driving apparatus includes an unshown control portion, and bends the bending portion 23a of the insertion portion 23 as an endoscope function in this case in the RL direction automatically in accordance with driving by an unshown driving motor provided in the operation portion main body 24.

On a side face on the opposite side to the UD angle knob 26 side on which the RL angular operation portion 40 is provided of the operation portion main body 24, a switch 29, a suction button 30 and an air/water feeding button 31 are provided so as to be arranged in a line along the longitudinal direction of the RL angular operation portion 40.

That is, the switch 29, the suction button 30 and the air/water feeding button 31 are provided so as to be aligned in a row in the vertical direction of the operation portion main body 24 at the side of the RL angular operation portion 40. Note that a switch 32 is provided on a side face of the operation portion main body 24 on the opposite side also.

The switch 29, the suction button 30 and the air/water feeding button 31 are each provided to the side of the UD angle knob 26 in an area in which, similarly to the RL angular operation portion 40, the components (switch 29, suction button 30 and air/water feeding button 31) can be operated by, for example, a forefinger or a middle finger of one hand of the operator in a state in which the operator grasps mainly the grip 25 in the palm of the one hand.

The configuration of the RL angular operation portion 40 of the present embodiment will now be described in detail.

As shown in FIG. 3, in the RL angular operation portion 40, an RL operation dial 42 as a first operation member that is an RL operation element which is located below the underside of a case body 41 that is fixed to the operation portion main body 24 is provided so as to be rotatable about a rotation axis X in the drawing.

In the RL operation dial 42, a dial rotation shaft 42a is extended so as to protrude from an upper portion of the RL operation dial 42. The dial rotation shaft 42a is rotatably housed inside the case body 41 in a state in which the dial rotation shaft 42a is maintained in a watertight state by an O-ring 41a provided in a lower face portion of the case body 41.

An initial position reversion mechanism portion 44 is provided inside the case body 41. The dial rotation shaft 42a is connected to the inside of the initial position reversion mechanism portion 44 from a lower portion side of the initial position reversion mechanism portion 44. A sensor rotation shaft 45a which is provided so as to pass through a potentiometer 45 that is a rotation detection sensor that is fixed inside the case body 41 is connected to the inside of the initial position reversion mechanism portion 44 from the upper side of the sensor rotation shaft 45a.

The initial position reversion mechanism portion 44 transmits a rotational force of the dial rotation shaft 42a to the sensor rotation shaft 45a, and also applies a rotational force that causes a rotational angle of the dial rotation shaft 42a and the sensor rotation shaft 45a to revert (return) to a set position against the aforementioned rotational force of the dial rotation shaft 42a. Note that, since the detailed configuration of the initial position reversion mechanism portion 44 is known, a description of the initial position reversion mechanism portion 44 is omitted herein.

The potentiometer 45 outputs an electrical signal that is based on a rotational angle (amount) of the sensor rotation shaft 45a to the RL driving apparatus. That is, in the RL angular operation portion 40 of the present embodiment, when the RL operation dial 42 is rotated, the dial rotation shaft 42a rotates, and the sensor rotation shaft 45a of the potentiometer 45 rotates via the initial position reversion mechanism portion 44.

At such time, the potentiometer 45 detects the rotational angle (amount) of the sensor rotation shaft 45a, and outputs an electrical signal to the RL driving apparatus. The electrical signal is output to the RL driving apparatus.

In the RL driving apparatus, the control portion (not shown) drivingly controls the RL driving motor in accordance with the electrical quantity of the electrical signal inputted from the potentiometer 45, to thereby bend the bending portion 23a of the insertion portion 23 in the RL direction.

That is, the RL operation dial 42 is configured to be capable of adjusting a bending amount in the RL direction of the bending portion 23a of the insertion portion 23 in accordance with the rotation amount.

In this case, if the RL operation dial 42 is rotated, for example, clockwise as viewed toward the lower part (distal end side) from the upper part (proximal end side) in the grip 25 direction from the operation portion main body 24, the bending portion 23a of the insertion portion 23 is bent in the R direction, and if the RL operation dial 42 is rotated counterclockwise, the bending portion 23a of the insertion portion 23 is bent in the L direction.

In addition, in the RL angular operation portion 40, an engagement portion 50 that is a switching mechanism which is configured to fix a rotational position of the RL operation dial 42 and fix/release a bending angle in the RL bending direction of the bending portion 23a of the insertion portion 23 is provided above (on the proximal end side of) the potentiometer 45 inside the case body 41.

The engagement portion 50 that is the switching mechanism includes an RL engagement lever 51 as a second operation member which is provided in a rotatable manner above (on the proximal end side of) a top surface of the case body 41, and which has a lever body 51a that extends in the short-side direction of the initial position reversion mechanism portion 44.

The RL engagement lever 51 is provided so as to be rotatable about a rotation axis X that is common with the rotation axis of the RL operation dial 42, and a lever rotation shaft 51b is housed inside the case body 41 in a state in which the lever rotation shaft 51b is maintained in a watertight state by an O-ring 41b provided in a top surface portion of the case body 41.

An outward flange 51c for slip prevention that contacts against the inner face of the top surface portion of the case body 41 is provided on the lever rotation shaft 51b. A first cam 52 having a cam surface 52a that serves as a first inclined surface portion formed on a lower end face is provided at an end portion of the lever rotation shaft 51b inside the case body 41.

At a lower portion (distal end side) of the first cam 52 inside the case body 41, a substantially tubular second cam 53 is provided on which a cam surface 53a that faces the cam surface 52a is formed as a second inclined surface portion on an upper end surface. A coned disc spring 54, a friction plate 55 and a cam guide 56 are housed in that order from the upper side (proximal end side) inside the second cam 53. Note that the cam guide 56 is fixed to the case body 41.

As shown in FIG. 4, a hole portion having a substantially rectangular cross-sectional shape is also formed in the second cam 53, and a cam guide 56 having a substantially rectangular cross-sectional shape that is a similar shape to the hole portion is inserted into the hole portion. By this means, the second cam 53 is configured to be movable in the vertical direction by the cam guide 56 without rotating.

Note that the aforementioned sensor rotation shaft 45a passes through the potentiometer 45 and protrudes from the upper portion of the potentiometer 45, and is inserted through the inside of a hole portion of the cam guide 56 in a rotatable condition so that an upper end face of the sensor rotation shaft 45a contacts a bottom face of the friction plate 55.

As shown in FIG. 5, in the RL angular operation portion 40 of the present embodiment configured as described above, when the RL engagement lever 51 is rotationally operated in a predetermined angle range of 0° to θ by an operator, the engagement portion 50 fixes the rotational position of the RL operation dial 42 and fixes/releases a bending angle in the RL bending direction of the bending portion 23a.

The angle of the RL engagement lever 51 is set so that, in an initial state of 0°, the RL engagement lever 51 causes the bending state in the RL direction of the bending portion 23a of the insertion portion 2 to revert completely to an initial position in which the bending portion 23a is a straight shape.

Further, the angle of the RL engagement lever 51 is set so that, in the initial state of θ, the RL engagement lever 51 fixes the bending state in the RL direction of the bending portion 23a of the insertion portion 2 so that the bending state does not automatically revert.

In this case, the engagement portion 50 is set so that, when the lever body 51a of the RL engagement lever 51 is at the initial position (position of θ/2 in the drawing), the engagement portion 50 fixes the bending state in the RL direction of the bending portion 23a at, for example, a bending angle of ±90°.

Specifically, the engagement portion 50 is set so as to fix the bending state in the RL direction of the bending portion 23a within a range from, for example, 0° that is a straight state to a maximum bending angle of ±180° when the lever body 51a of the RL engagement lever 51 is rotationally operated from the initial position (0° position in the drawing) in a predetermined one direction to a first maximum rotational position of a predetermined angle θ shown on the upper side (proximal end side) as viewed from the front of the sheet in FIG. 5.

Further, the engagement portion 50 is set so as not to fix (i.e. to release) the bending state in the RL direction of the bending portion 23a when the lever body 51a of the RL engagement lever 51 is rotationally operated to a second maximum rotational position in a predetermined other direction toward the initial position (0° position in the drawing) that is shown in this case on the lower side (distal end side) as viewed from the front of the sheet in FIG. 5.

In addition, when the lever body 51a of the RL engagement lever 51 is at the initial position (position denoted by θ/2 in the drawing), the engagement portion 50 is in a state in which the engagement portion 50 receives predetermined frictional resistance from the friction plate 55 that contacts the upper end surface of the sensor rotation shaft 45a of the potentiometer 45.

At such time, rotation of the sensor rotation shaft 45a is restrained by a rotational force that is applied from the initial position reversion mechanism portion 44 in accordance with the predetermined frictional resistance from the friction plate 55.

In this state, the sensor rotation shaft 45a of the potentiometer 45 is in a state in which the sensor rotation shaft 45a is restrained at a rotational angle at which the sensor rotation shaft 45a outputs to the RL driving apparatus an electrical signal for making the bending state in the RL direction of the bending portion 23a, for example, a bending angle of ±90°.

Note that, in this state, if the operator performs a rotational operation of the RL operation dial 42 to cause the bending state in the RL direction of the bending portion 23a to bend to, for example, an angle that is ±90° or more and releases the finger that is operating the RL operation dial 42, the sensor rotation shaft 45a will rotate and return (revert) as far as the position at which the bending state in the RL direction of the bending portion 23a becomes, for example, a bending angle of ±90°, by means of a rotational force that is applied from the initial position reversion mechanism portion 44.

Thus, by setting the rotational position of the lever body 51a of the RL engagement lever 51 in advance to the position denoted by θ/2 in the drawing, during a bending operation in which the RL bending angle of the bending portion 23a is, for example, between ±90° and ±180°, by releasing the finger that is operating the RL operation dial 42, the operator can cause the bending angle in the RL direction of the bending portion 23a to, for example, automatically revert to ±90°. It is possible to realize the function by setting a rotational force of the neutral-return mechanism portion 44 that is applied to the sensor rotation shaft 45a and a resistance force that is applied to the sensor rotation shaft 45a by the friction plate 55 and the O-ring 41a to be in balance with each other when the lever body 51a is at the rotational position denoted by θ/2 in the drawing.

In addition, in the engagement portion 50, the first cam 52 rotates as illustrated in FIG. 6 when the lever body 51a of the RL engagement lever 51 is rotationally operated as far as the predetermined angle θ.

At such time, in the engagement portion 50, the second cam 53 is pushed downward (toward the distal end side) as a result of the first cam 52 rotating. That is, when the first cam 52 rotates, the second cam 53 moves downward (toward the distal end side) based on a so-called "swash plate cam" principle whereby the cam surface 52a pushes down the cam surface 53a of the second cam 53.

In accompaniment with the move, the coned disc spring 54 provided inside the second cam 53 is also pushed downward (toward the distal end side), and the friction plate 55 presses the upper end surface of the sensor rotation shaft 45a of the potentiometer 45.

As a result, frictional resistance arises that is generated by the pressing force from the friction plate 55, and rotation of the sensor rotation shaft 45a in a reverting direction against the rotational force applied from the initial position reversion mechanism portion 44 is restrained.

In this state, even if the operator releases the finger that is operating the RL operation dial 42, the RL operation dial 42 is kept stationary.

Note that, even in the state in which the RL operation dial 42 is kept stationary, the operator can also perform a rotational operation of the RL operation dial 42 against the frictional resistance that the sensor rotation shaft 45a receives from the friction plate 55.

Therefore, the operator can fix the bending state in the RL direction of the bending portion 23a at a desired bending angle within a range of, for example, 0° to ±180°.

On the other hand, in the engagement portion 50, if the lever body 51a of the RL engagement lever 51 is rotationally operated until the rotational position of the lever body 51a is the initial position (0° position in the drawing), the first cam 52 rotates and a force pushing down the second cam 53 decreases, and the second cam 52 receives the urging force of the coned disc spring 54 and moves upward (toward the proximal end side).

In this state, as shown in FIG. 3, in the engagement portion 50, the cam surface 53a of the second cam 53 facing the cam surface 52a of the first cam 52 enters a substantially surface contact state, and a state is entered in which the friction plate 55 simply contacts the upper end surface of the sensor rotation shaft 45a of the potentiometer 45.

That is, a state is entered in which a pressing force from the friction plate 55 onto the upper end surface of the sensor rotation shaft 45a of the potentiometer 45 is released and frictional resistance received from the friction plate 55 substantially disappears and the sensor rotation shaft 45a can freely rotate.

Therefore, after rotationally operating the RL operation dial 42 in a predetermined direction, if the operator releases the finger that is operating the RL operation dial 42, the sensor rotation shaft 45a returns to a predetermined reversion position by means of the rotational force applied from the initial position reversion mechanism portion 44.

In a state in which the sensor rotation shaft 45a has returned to the predetermined reversion position in this manner, the sensor rotation shaft 45a is driven to the initial position at which the bending angle in the RL direction of the bending portion 23a becomes 0° and becomes a straight shape that does not bend.

In addition, by rotating the lever body 51a of the RL engagement lever 51 within an angle range from the initial position (0° position in the drawing) to the predetermined angle θ, the operator can vary the frictional resistance that the sensor rotation shaft 45a receives from the friction plate 55.

Therefore, the operator can set so as to cause bending in the RL direction of the bending portion 23a to revert steplessly to an arbitrary angle in a range of, for example, 0° to ±180° in accordance with the rotational angle of the lever body 51a of the RL engagement lever 51 when the operator releases the finger that is operating from the RL operation dial 42.

As described above, the endoscope 2 of the present embodiment has a configuration such that, by performing a rotational operation of the lever body 51a of the RL engagement lever 51, an operator can, at will, switch on or off a reversion function whereby the bending portion 23a returns as far as a position that is at a predetermined bending angle when the operator releases the hand from the RL operation dial 42.

That is, by rotationally operating the lever body 51a of the RL engagement lever 51 as far as a predetermined angle θ in advance, the operator can rotationally operate the RL operation dial 42 and continuously fix (maintain) the bending state of the bending portion 23a that is bent at the predetermined angle even after the operator releases the hand from the RL operation dial 42, without the necessity of continuously pressing the RL operation dial 42 with a finger.

Further, by rotationally operating the lever body 51a of the RL engagement lever 51 as far as the initial position (0° position in the drawing) in advance, after rotationally operating the RL operation dial 42, the operator can cause the bending portion 23a to automatically revert to the initial position by releasing the hand from the RL operation dial 42.

In addition, by rotationally operating the lever body 51a of the RL engagement lever 51 to an arbitrary angle from 0° to θ in advance, after rotationally operating the RL operation dial 42, the operator can cause the bending portion 23a to automatically revert to a bending state at the arbitrary angle by releasing the hand from the RL operation dial 42.

Note that, in the engagement portion 50 provided in the endoscope 2 of the present embodiment, as shown in FIG. 7 and FIG. 8, the operating range of the RL engagement lever 51 is set so as to be outside the closest operating range of the UD angle knob 26, the UD knob engagement lever 28 and the switch 29 which correspond to a third operation member.

More specifically, the operating range of the RL engagement lever 51 is set so that the lever body 51a does not enter into a closest plane of the operating range of the UD angle knob 26 that is indicated by an alternate long and short dash line A in the drawing, does not enter into a closest plane of the operating range of the UD knob engagement lever 28 that is indicated by an alternate long and short dash line B in the drawing, and does not enter into a closest plane of the operating range of the switch 29 that is indicated by an alternate long and short dash line C in the drawing.

Note that the alternate long and short dash line B indicates an operating range with which the UD knob engagement lever 28 does not interfere, at a height position in the vertical direction of the RL engagement lever 51 in a direction viewed from the front of the sheet in FIG. 2.

That is, the operating range of the RL engagement lever 51 is set so that not only does the lever body 51a not interfere with the UD angle knob 26, the UD knob engagement lever 28 and the switch 29, but also so that the lever body 51a does not interfere with a finger of the operator when operating the UD angle knob 26 and the UD knob engagement lever 28.

By this means, when an operation of the lever body 51a of the RL engagement lever 51 is being performed, the UD angle knob 26, the UD knob engagement lever 28 and the switch 29 do not become a hindrance, and furthermore, when operating the UD angle knob 26, the UD knob engagement lever 28 or the switch 29, the lever body 51a does not become a hindrance, and thus a decrease in the operability of each of the components is also prevented.

MODIFICATION

A modification described hereunder may be adopted for the above-described endoscope 2, and in particular for the RL angular operation portion 40.

The endoscope 2 of the present modification has a configuration in which, as shown in FIG. 9 and FIG. 10, the position of the RL engagement lever 51 provided in the engagement portion 50 of the RL angular operation portion 40 is at a central portion in the longitudinal direction (vertical direction) of the case body 41.

In this case, in the engagement portion 50, as shown in FIG. 9, the RL engagement lever 51 and the first cam 52 are formed as one body, and the sensor rotation shaft 45a is inserted through the RL engagement lever 51 and the first cam 52.

A cylindrical portion of the RL engagement lever 51 that protrudes vertically is maintained in a watertight state by an O-ring 41b, and is pivotally supported in a rotatable manner with respect to the case body 41.

The lever body 51a of the RL engagement lever 51 is arranged so as to extend from a slit-shaped hole portion 46 formed at a position that is at the middle of the case body 41 (see FIG. 10).

Further, an outward flange 45b is provided partway along the sensor rotation shaft 45a. The outward flange 45b is arranged between the friction plate 55 that faces the top surface of the outward flange 45b and applies frictional resistance to the outward flange 45b, and the cam guide 56 that faces the bottom surface of the outward flange 45b.

The friction plate 55 according to the present modification includes a hole portion through which the sensor rotation shaft 54 is inserted. Note that in this case the potentiometer 45 is provided at a position that is further on the upper side (proximal end side) than the RL engagement lever 51.

In the engagement portion 50 of the present modification, when the RL engagement lever 51 is rotationally operated and the second cam 53 is pushed downward (toward the distal end side) by the first cam 52, the friction plate 55 presses the top surface of the outward flange 45b of the sensor rotation shaft 45a through the coned disc spring 54 to thereby generate frictional resistance.

Consequently, rotation of the sensor rotation shaft 45a in a reverting direction against the rotational force applied from the initial position reversion mechanism portion 44 is restrained. The other components and actions are the same as in the above described embodiment.

Further, as shown in FIG. 10, the lever body 51a of the RL engagement lever 51 is provided so as to extend from the hole portion 46 in the case body 41 at a position along the horizontal direction between the suction button 30 and the air/water feeding button 31.

Consequently, the operating range of the lever body 51a of the RL engagement lever 51 is set to be outside the operating range of the UD angle knob 26, the UD knob engagement lever 28 and the switch 29 that are provided on the operation portion main body 24, and to also be outside of the operating range of the suction button 30 and the air/water feeding button 31.

In the endoscope 2 of the present modification configured as described above, by providing the RL engagement lever 51 of the engagement portion 50 of the RL angular operation portion 40 at a position that is partway along the RL angular operation portion 40, it is easier for a forefinger or middle finger of the operator to reach the RL engagement lever 51, and thus the accessibility when operating the components is improved.

In addition, the operating range of the RL engagement lever 51 is set so that not only does the lever body 51a not interfere with the UD angle knob 26, the UD knob engagement lever 28 and the switch 29, but also so that the lever body 51a does not interfere with a finger of the operator when operating the UD angle knob 26 and the UD knob engagement lever 28.

By this means, when an operation of the lever body 51a of the RL engagement lever 51 is being performed, the UD angle knob 26, the UD knob engagement lever 28, the switch 29, the suction button 30 and the air/water feeding button 31 do not become a hindrance, and furthermore, when an operation of the UD angle knob 26, the UD knob engagement lever 28, the switch 29, the suction button 30 or the air/water feeding button 31 is being performed, the lever body 51a does not become a hindrance, and thus a decrease in the operability of each of the components is also prevented.

Second Embodiment

A second embodiment of the present invention will now be described with reference to the accompanying drawings. Note that components that have been described in the first embodiment are denoted by the same reference numerals, and a detailed description of the components is omitted hereunder.

Figure 11:
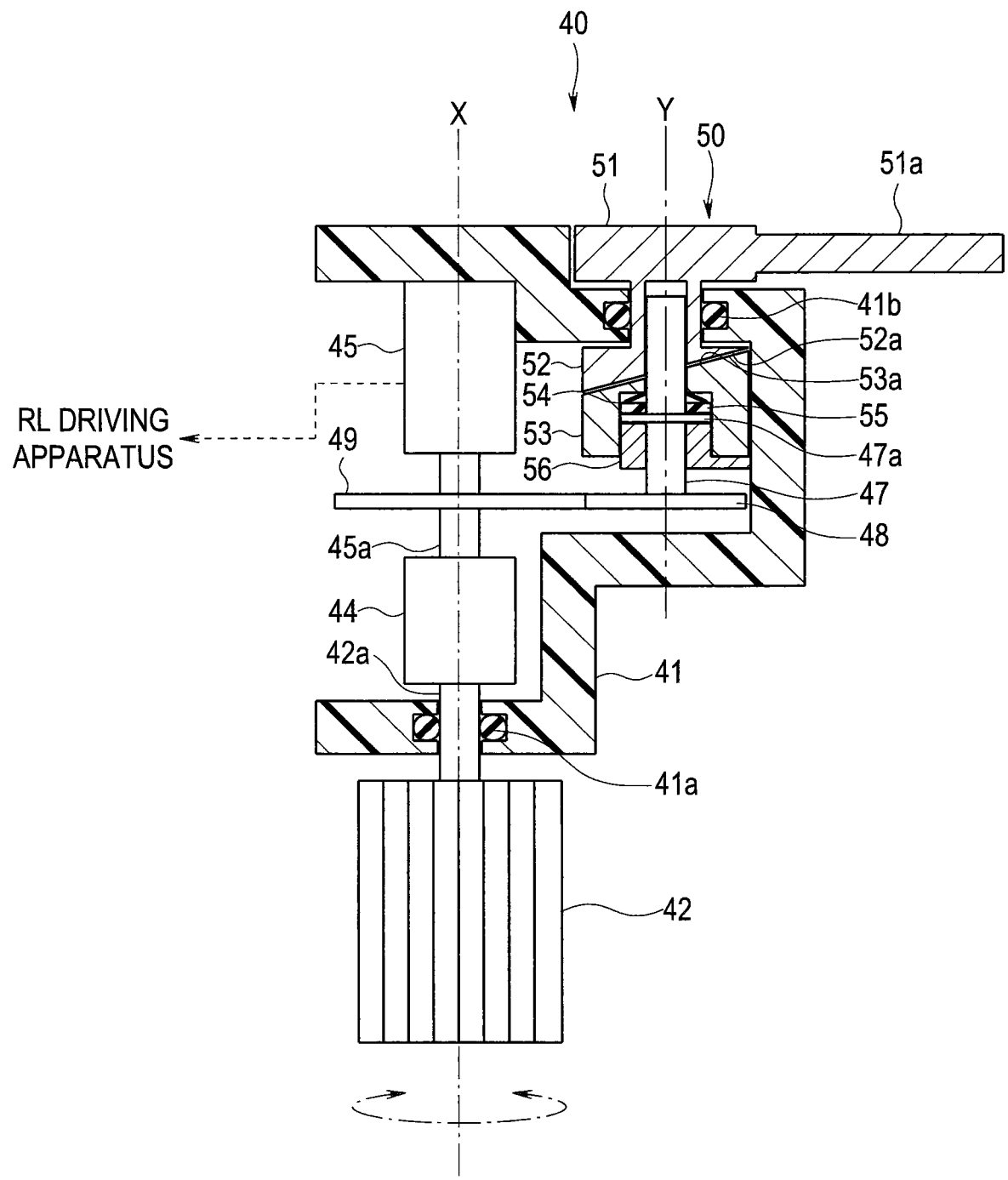
FIG. 11 is a cross-sectional view illustrating the configuration of an RL angular operation portion of a second embodiment according to the present invention.
Figure 12:
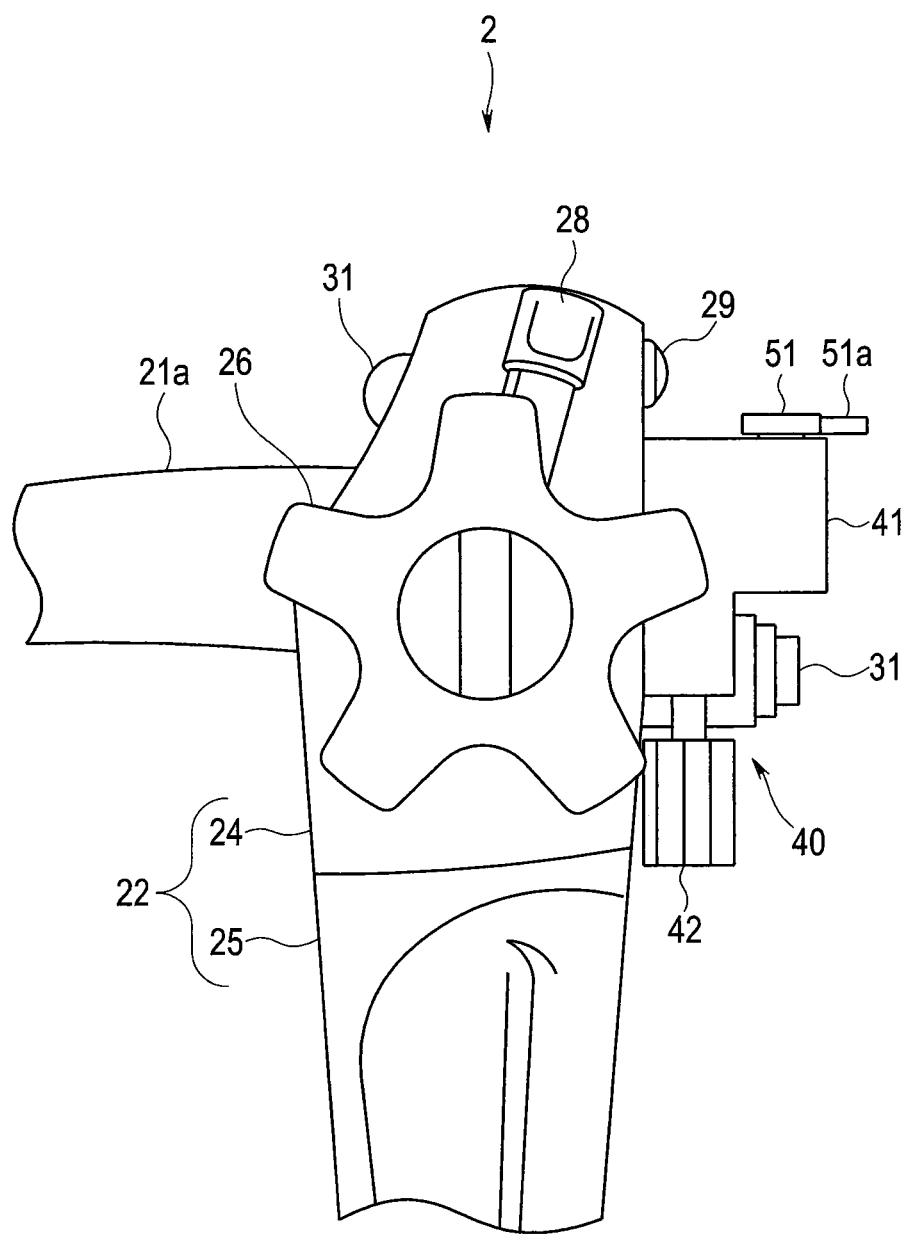
FIG. 12 is a side view illustrating an operation portion in which the RL angular operation portion is provided of the second embodiment according to the present invention.
Figure 13:
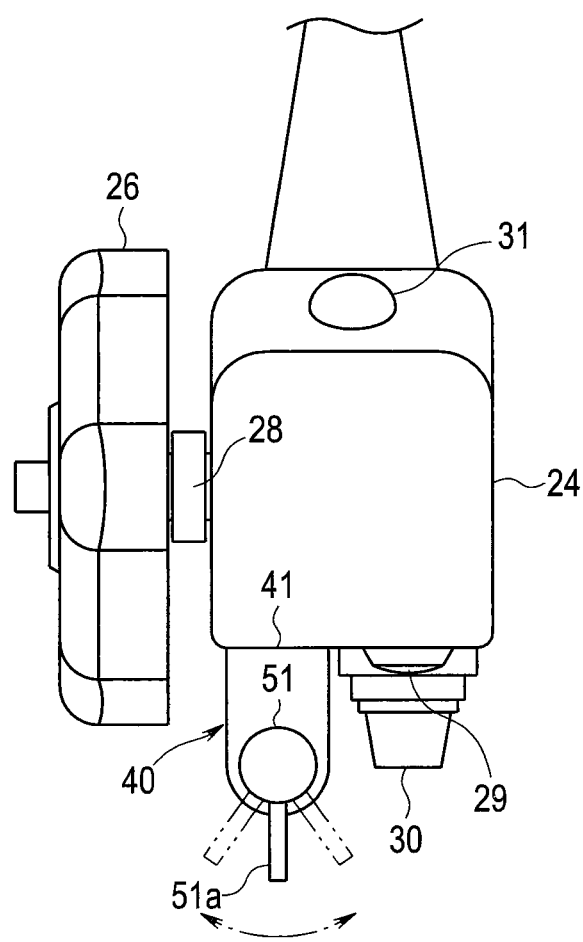
FIG. 13 is a top view illustrating the operation portion in which the RL angular operation portion is provided of the second embodiment according to the present invention.
Figure 14:
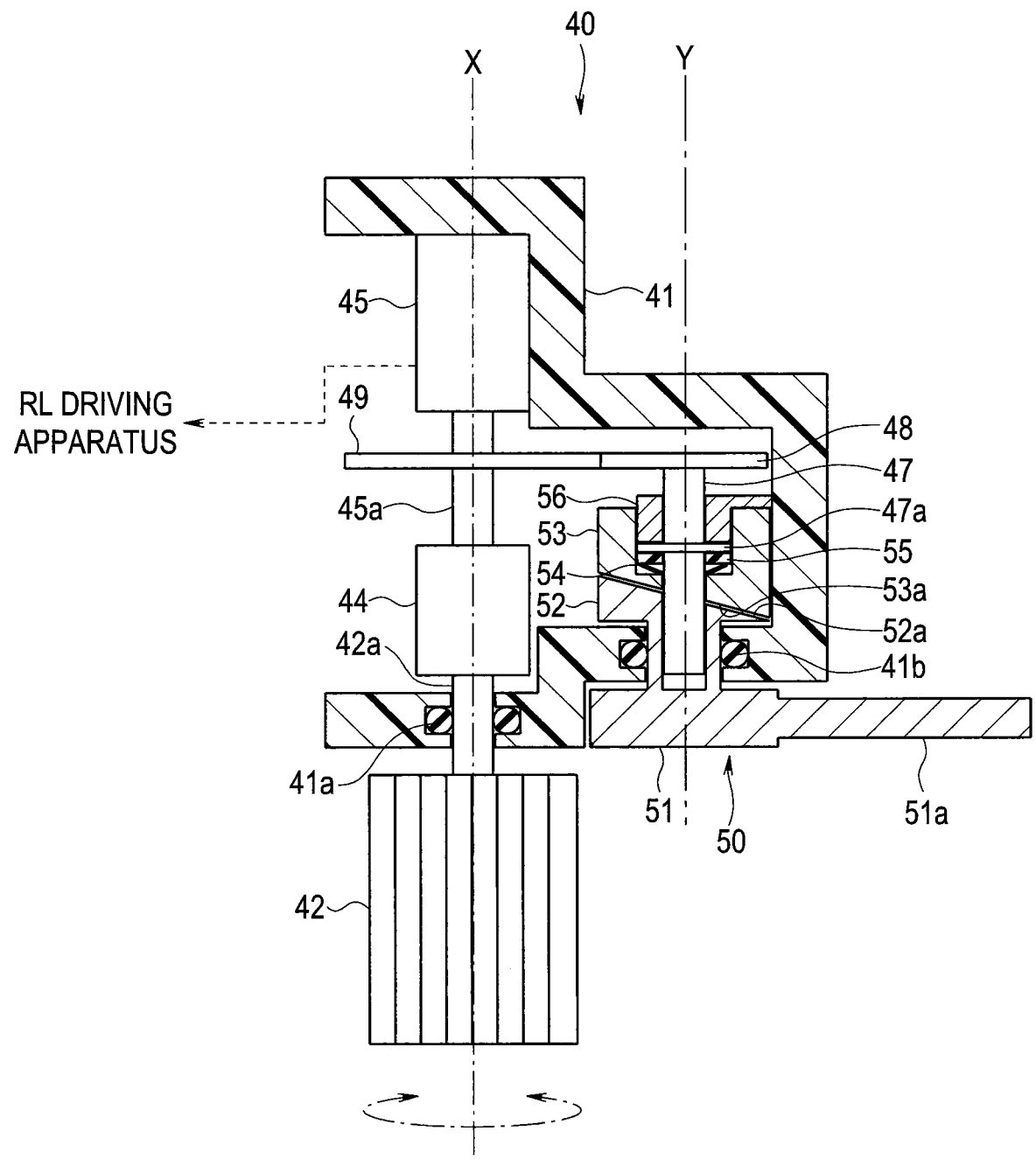
FIG. 14 is a cross-sectional view illustrating the configuration of an RL angular operation portion of a first modification of the second embodiment according to the present invention.
Figure 15:
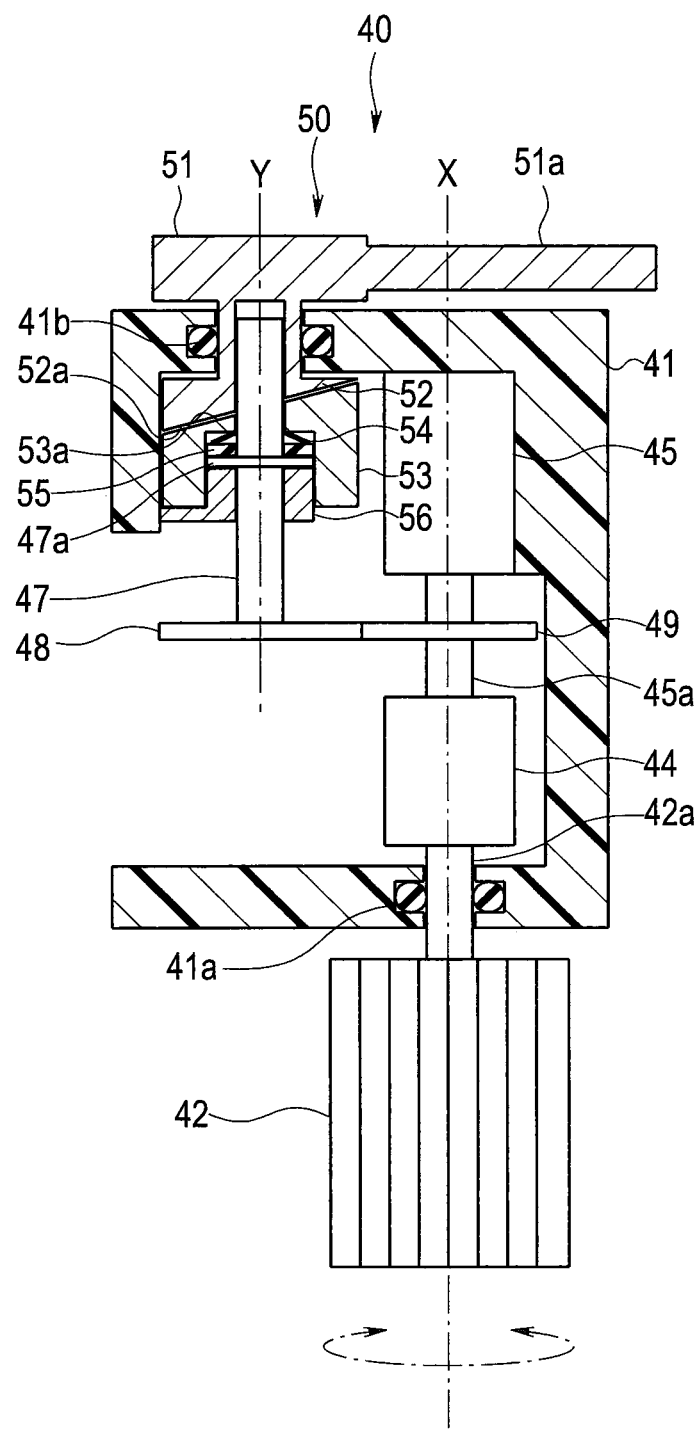
FIG. 15 is a cross-sectional view illustrating the configuration of an RL angular operation portion of a second modification of the second embodiment according to the present invention.
Figure 16:
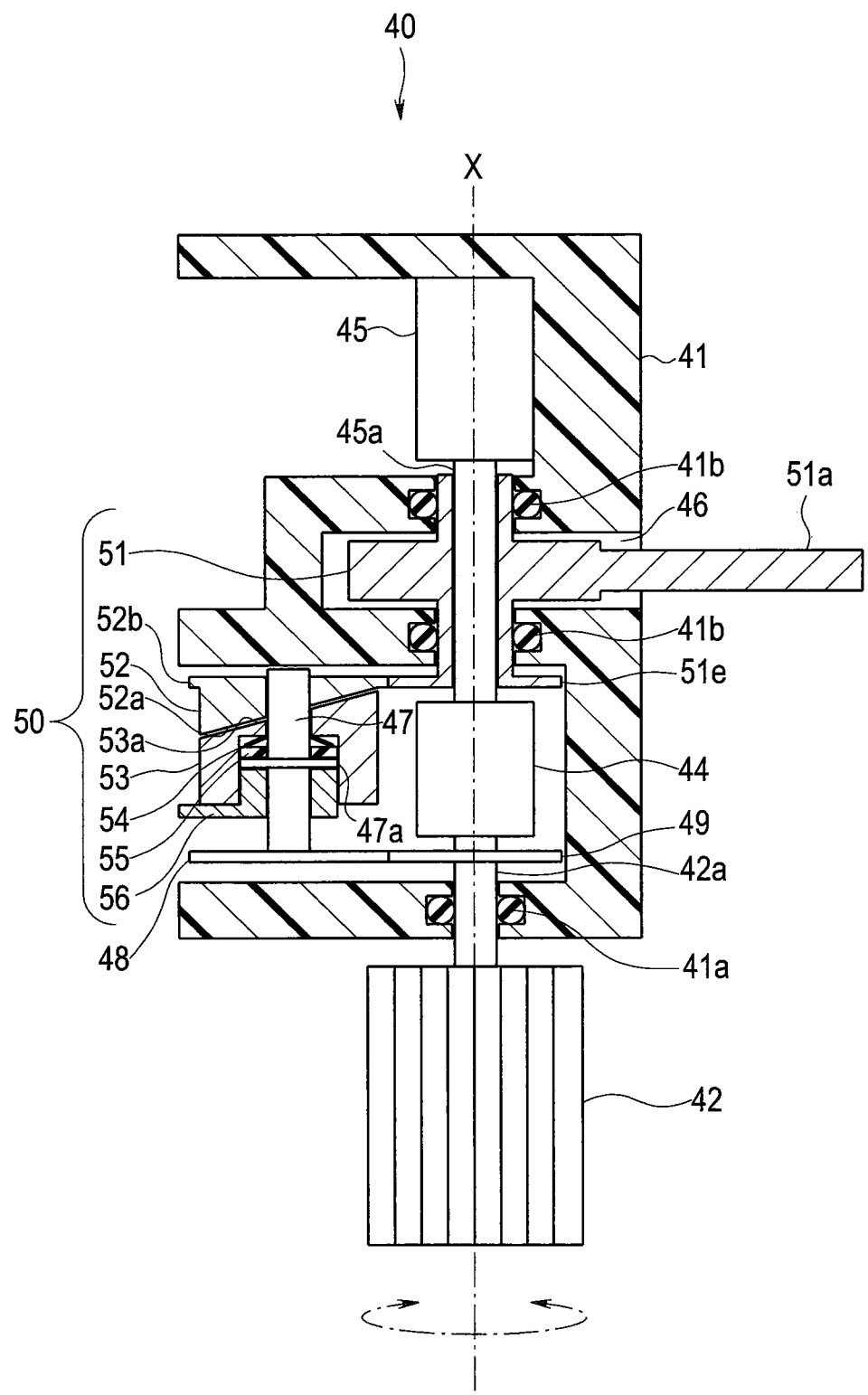
FIG. 16 is a cross-sectional view illustrating the configuration of an RL angular operation portion of a third modification of the second embodiment according to the present invention.
Figure 17:
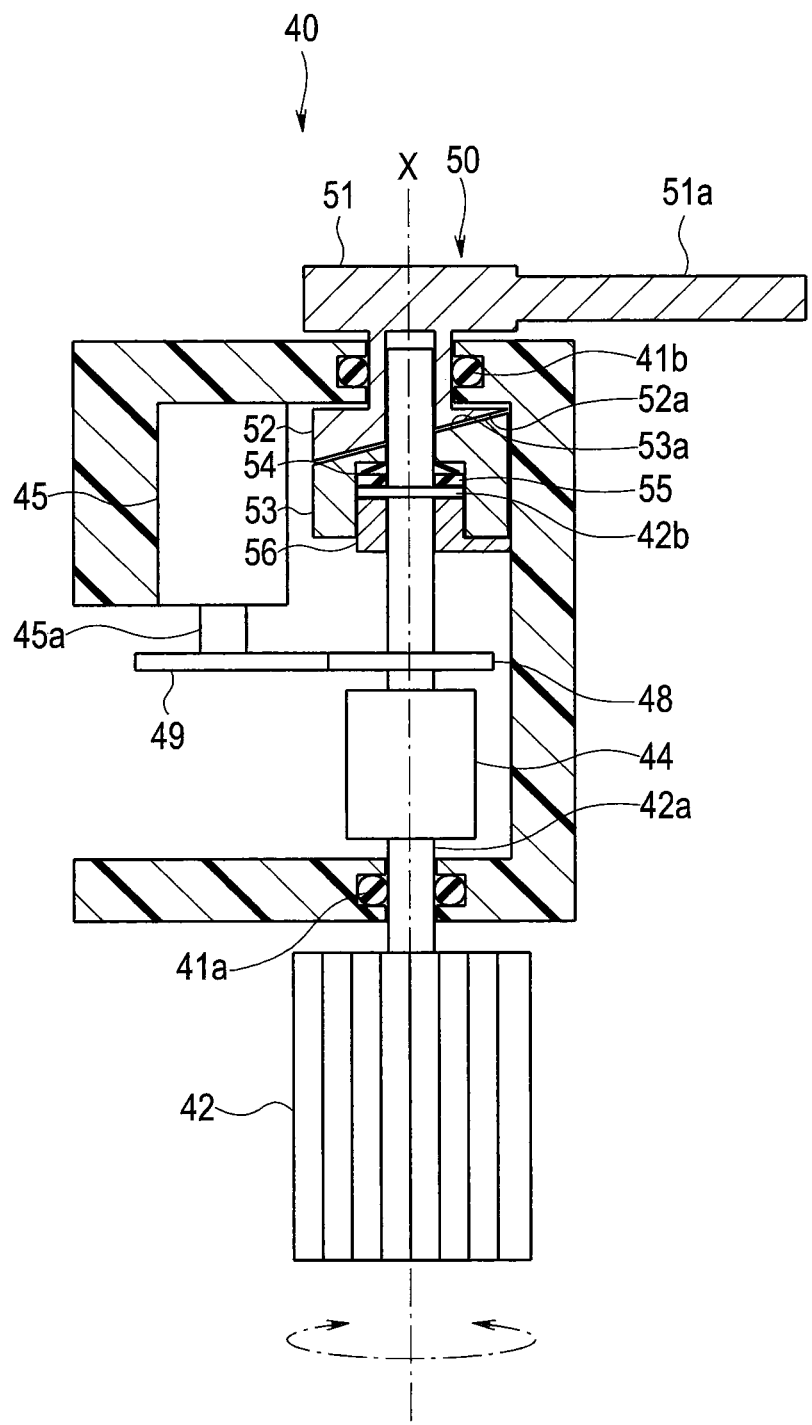
FIG. 17 is a cross-sectional view illustrating the configuration of an RL angular operation portion of a fourth modification of the second embodiment according to the present invention.

FIG. 11 to FIG. 17 relate to a second embodiment of the present invention. FIG. 11 is a cross-sectional view illustrating the configuration of an RL angular operation portion. FIG. 12 is a side view illustrating an operation portion in which the RL angular operation portion is provided. FIG. 13 is a top view illustrating the operation portion in which the RL angular operation portion is provided. FIG. 14 is a cross-sectional view illustrating the configuration of an RL angular operation portion according to a first modification. FIG. 15 is a cross-sectional view illustrating the configuration of an RL angular operation portion according to a second modification. FIG. 16 is a cross-sectional view illustrating the configuration of an RL angular operation portion according to a third modification. FIG. 17 is a cross-sectional view illustrating the configuration of an RL angular operation portion according to a fourth modification.

As shown in FIG. 11, the endoscope 2 of the present embodiment has a configuration in which the position of the engagement portion 50 of the RL angular operation portion 40 is shifted away from the operation portion main body 24 in a direction that is orthogonal to the longitudinal direction (vertical direction) of the case body 41.

That is, the RL angular operation portion 40 has a rotation axis Y of the RL engagement lever 51 of the engagement portion 50 which is different to the rotation axis X of the RL operation dial 42, and which is located further away from the operation portion main body 24 than the rotation axis X. Note that the rotation axis X and the rotation axis Y are parallel axes.

More specifically, in the engagement portion 50 of the present embodiment, the RL engagement lever 51 and the first cam 52 are formed as one body, and a cam shaft 47 is inserted in a rotatable condition through the RL engagement lever 51 and the first cam 52.

A cylindrical portion of the RL engagement lever 51 that extends downward (toward the distal end side) and is connected with the first cam 52 is maintained in a watertight state by the O-ring 41b, and is pivotally supported in a rotatable manner with respect to the case body 41.

Further, an outward flange 47a is provided partway along the cam shaft 47. The outward flange 47a is arranged between the friction plate 55 that faces the top surface of the outward flange 47a and applies frictional resistance to the outward flange 47a, and the cam guide 56 that faces the bottom surface of the outward flange 47a. In the embodiment, the friction plate 55 includes a hole portion through which a sensor rotation shaft 54 is inserted.

A spur gear 48 is provided at a lower end of the cam shaft 47. The gear 48 is meshed with a spur gear 49 provided partway along the sensor rotation shaft 45a. By this means, rotation and stopping of the cam shaft 47 and the sensor rotation shaft 45a are transmitted to each other.

In the engagement portion 50 of the present embodiment, when the RL engagement lever 51 is rotationally operated and the second cam 53 is pushed downward (toward the distal end side) by the first cam 52, the friction plate 55 presses the top surface of the outward flange 47a of the cam shaft 47 through the coned disc spring 54 to thereby generate frictional resistance. Consequently, the cam shaft 47 is restrained without being rotated by the friction plate 55.

At such time, rotation in a reverting direction against the rotational force applied from the initial position reversion mechanism portion 44 that is applied to the sensor rotation shaft 45a is also restrained since the gear 48 of the cam shaft 47 and the gear 49 of the sensor rotation shaft 45a are intermeshing. Note that the other components and actions are the same as in the above described first embodiment.

With the above-described endoscope 2 of the present embodiment also, an operator can easily switch between a state in which the bending state of the bending portion 23a that is bent to a predetermined angle when the operator rotationally operates the RL operation dial 42 is fixed (maintained) even when the operator releases the hand from the RL operation dial 42, and a state in which the bending portion 23a returns as far as a position that is at a predetermined bending angle when the operator releases the hand from the RL operation dial 42.

That is, similarly to the first embodiment, the endoscope 2 of the present embodiment is also configured so that, by a rotational operation of the lever body 51a of the RL engagement lever 51, the operator can, at will, switch on or off a reversion function whereby the bending portion 23a returns as far as a position at a predetermined bending angle upon the operator releasing the hand from the RL operation dial 42.

Further, as shown in FIG. 12 and FIG. 13, in the RL angular operation portion 40 in this case, in comparison to the configuration described in the first embodiment, the lever body 51a of the RL engagement lever 51 of the engagement portion 50 is provided so as to extend from a position that is away from the operation portion main body 24.

Thus, the operating range of the lever body 51a of the RL engagement lever 51 can be set to be outside of the operating range of the UD angle knob 26, the UD knob engagement lever 28 and the switch 29 that are provided on the operation portion main body 24.

In the endoscope 2 of the present embodiment that is configured as described above, because the RL angular operation portion 40 provided in the operation portion main body 24 has a configuration in which the rotation axis X of the RL operation dial 42 and the rotation axis Y of the RL engagement lever 51 of the engagement portion 50 are at different positions, the length in the vertical direction of the endoscope 2 can be shortened, and a distance between the RL operation dial 42 and the lever body 51a of the RL engagement lever 51 can also be shortened.

Thus, it is easier for a forefinger or middle finger of the operator to reach both of the RL operation dial 42 and the RL engagement lever 51, and the accessibility when operating the components is improved.

In addition, the lever body 51a of the RL engagement lever 51 is provided at a position that is separated from the operation portion main body 24, and therefore the UD angle knob 26, the UD knob engagement lever 28, the switch 29, the suction button 30 and the air/water feeding button 31 do not become a hindrance, and furthermore the lever body 51a does not become a hindrance when operating the UD angle knob 26, the UD knob engagement lever 28, the switch 29, the suction button 30 and the air/water feeding button 31, and thus the operability of each of the components is also improved.

MODIFICATIONS

The configurations of the various modifications described hereunder may be adopted for the above-described endoscope 2, and in particular for the RL angular operation portion 40.

First Modification

As shown in FIG. 14, in the RL angular operation portion 40, the RL engagement lever 51 of the engagement portion 50 may be provided on the lower side (distal end side) of the case body 41 in the vicinity of the RL operation dial 42, at a position that is away from the operation portion main body 24.

Thus, in the RL angular operation portion 40, by providing the RL engagement lever 51 of the engagement portion 50 at a lower position that is on the distal end side of the endoscope 2, similarly to the RL operation dial 42, it becomes still easier for a forefinger or middle finger of the operator to reach the RL engagement lever 51, and the accessibility when operating the components can be improved.

Second Modification

As shown in FIG. 15, in the RL angular operation portion 40, as a configuration in which the rotation axis X of the RL operation dial 42 and the rotation axis Y of the RL engagement lever 51 of the engagement portion 50 are at different positions, the RL operation dial 42 may be provided at a position that is away from the operation portion main body 24, and the RL engagement lever 51 of the engagement portion 50 may be provided at a position that is close to the operation portion main body 24.

Third Modification

As shown in FIG. 16, in the RL angular operation portion 40, as a configuration in which the rotation axis X of the RL operation dial 42 and a rotation axis (X) of the RL engagement lever 51 of the engagement portion 50 are at the same position, the RL operation dial 42 and the RL engagement lever 51 may be provided at positions that are away from the operation portion main body 24, and furthermore, the RL engagement lever 51 may be provided at a position at a center portion in the longitudinal direction (vertical direction) of the case body 41 by a configuration similar to the configuration of the modification of the first embodiment.

Further, in this case, in the RL angular operation portion 40, a cam mechanism including the first cam 52 and the second cam 53 is provided at a position that is closer to the operation portion main body 24 than the RL operation dial 42 and the RL engagement lever 51 are to the operation portion main body 24.

Note that a spur gear 51e is provided at a lower end portion of the RL engagement lever 51, and a spur gear 52b that meshes with the gear 51e is provided at an upper end portion of the first cam 52. By this means, the configuration is one in which rotation of the RL engagement lever 51 is transmitted to the first cam 52.

Fourth Modification

As shown in FIG. 17, in the RL angular operation portion 40, as a configuration in which the rotation axis X of the RL operation dial 42 and a rotation axis (X) of the RL engagement lever 51 of the engagement portion 50 are at the same position, the RL operation dial 42 and the RL engagement lever 51 may be provided at positions that are away from the operation portion main body 24, and the potentiometer 45 may be provided at a position that is closer to the operation portion main body 24 than the RL operation dial 42 and the RL engagement lever 51.

Third Embodiment

A third embodiment of the present invention will now be described with reference to the accompanying drawings. Note that components described in each of the foregoing embodiments are denoted by the same reference numerals, and a detailed description of the components is omitted hereunder.

Figure 18:
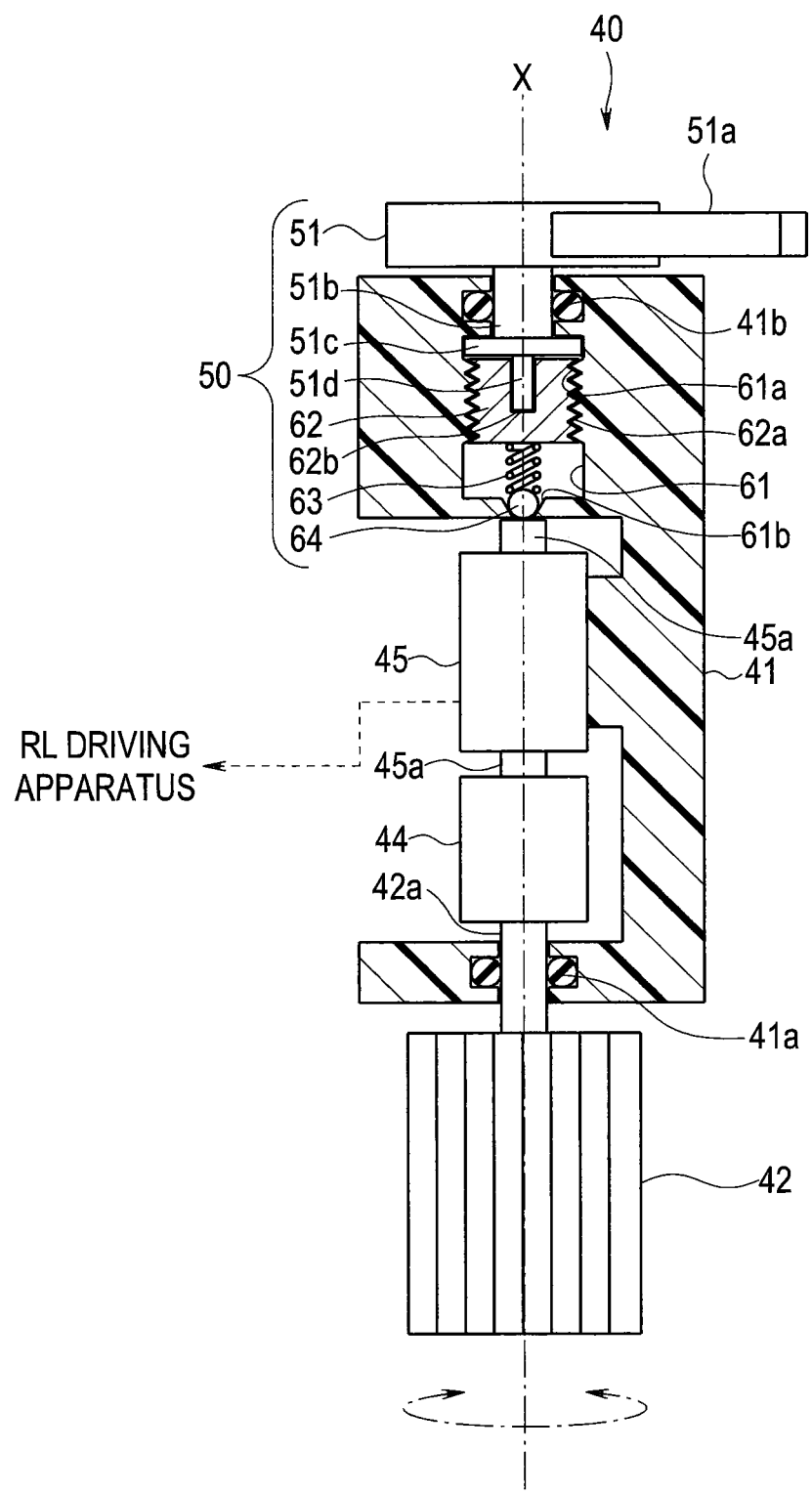
FIG. 18 is a cross-sectional view illustrating the configuration of an RL angular operation portion of a third embodiment according to the present invention.
Figure 19:
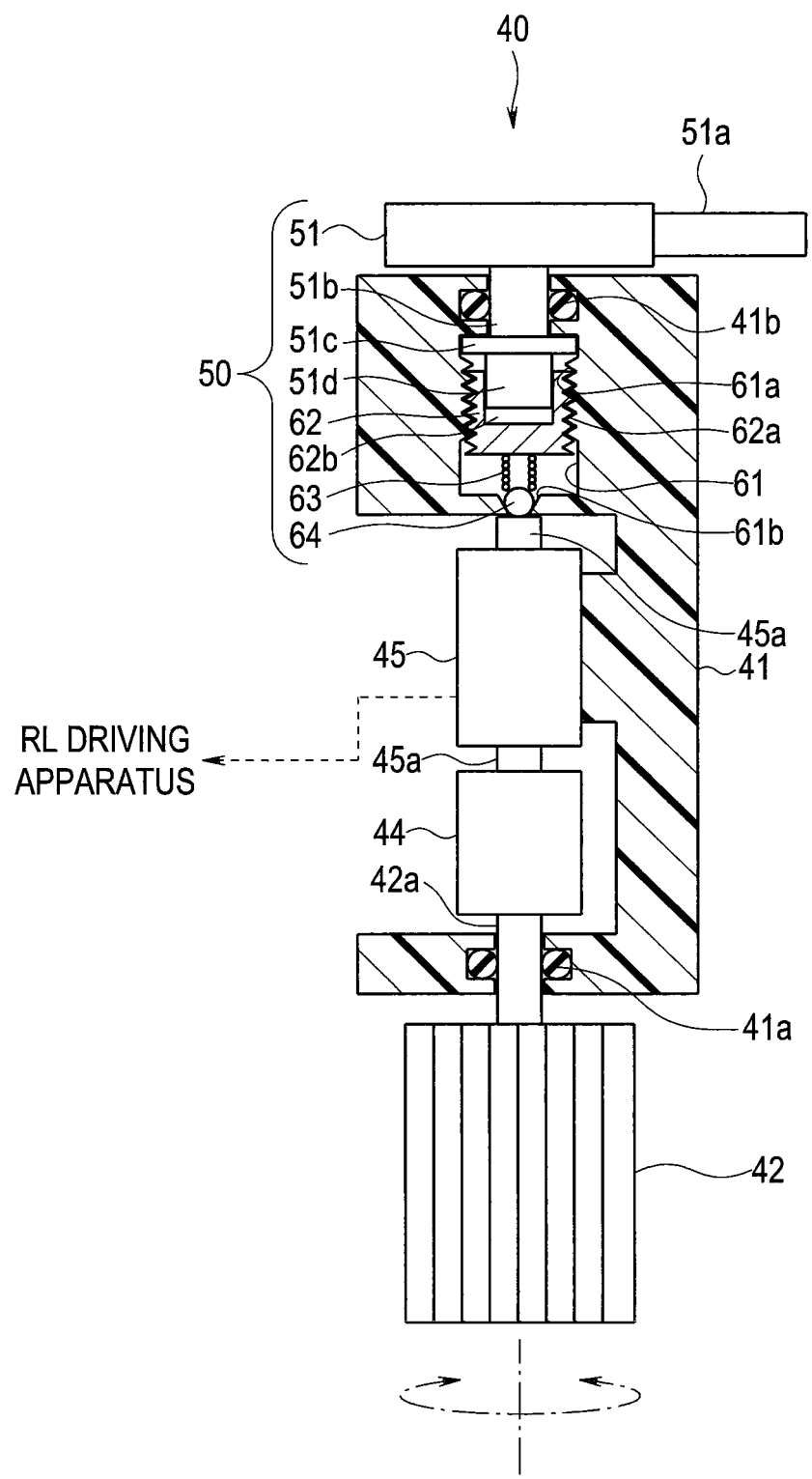
FIG. 19 is a cross-sectional view for describing an action of the RL angular operation portion of the third embodiment according to the present invention.
Figure 20:
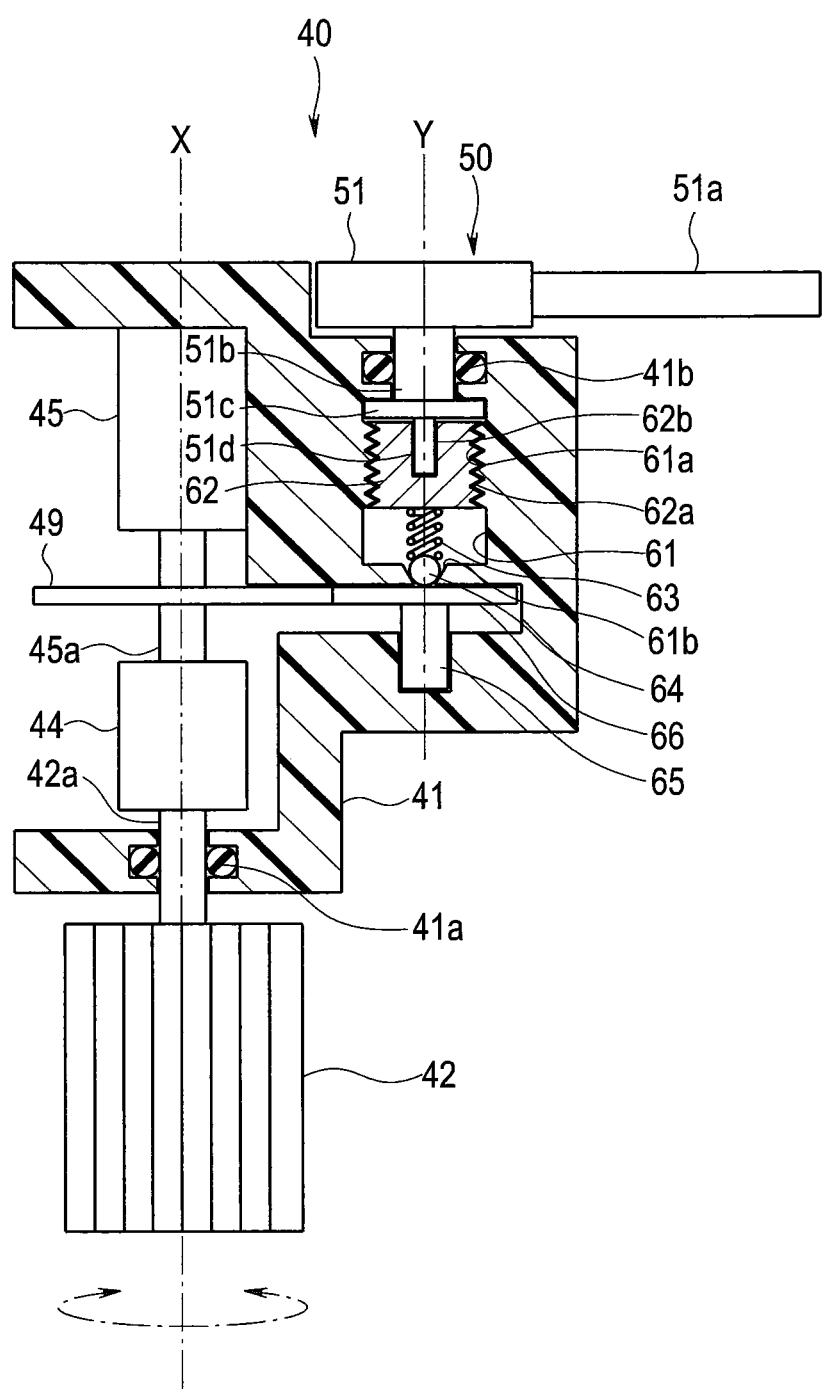
FIG. 20 is a cross-sectional view illustrating the configuration of an RL angular operation portion of a first modification of the third embodiment according to the present invention.
Figure 21:
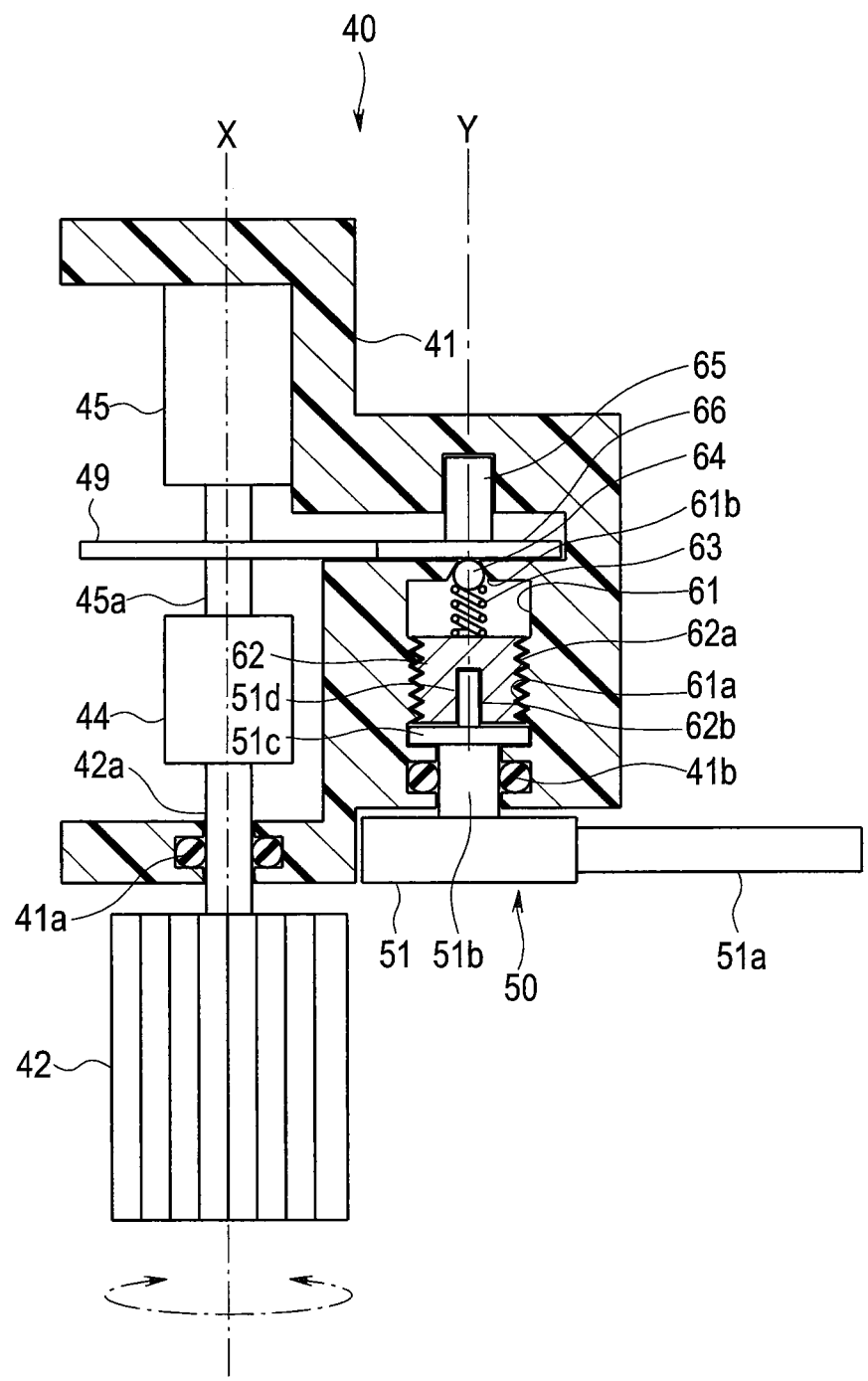
FIG. 21 is a cross-sectional view illustrating the configuration of an RL angular operation portion of a second modification of the third embodiment according to the present invention.
Figure 22:
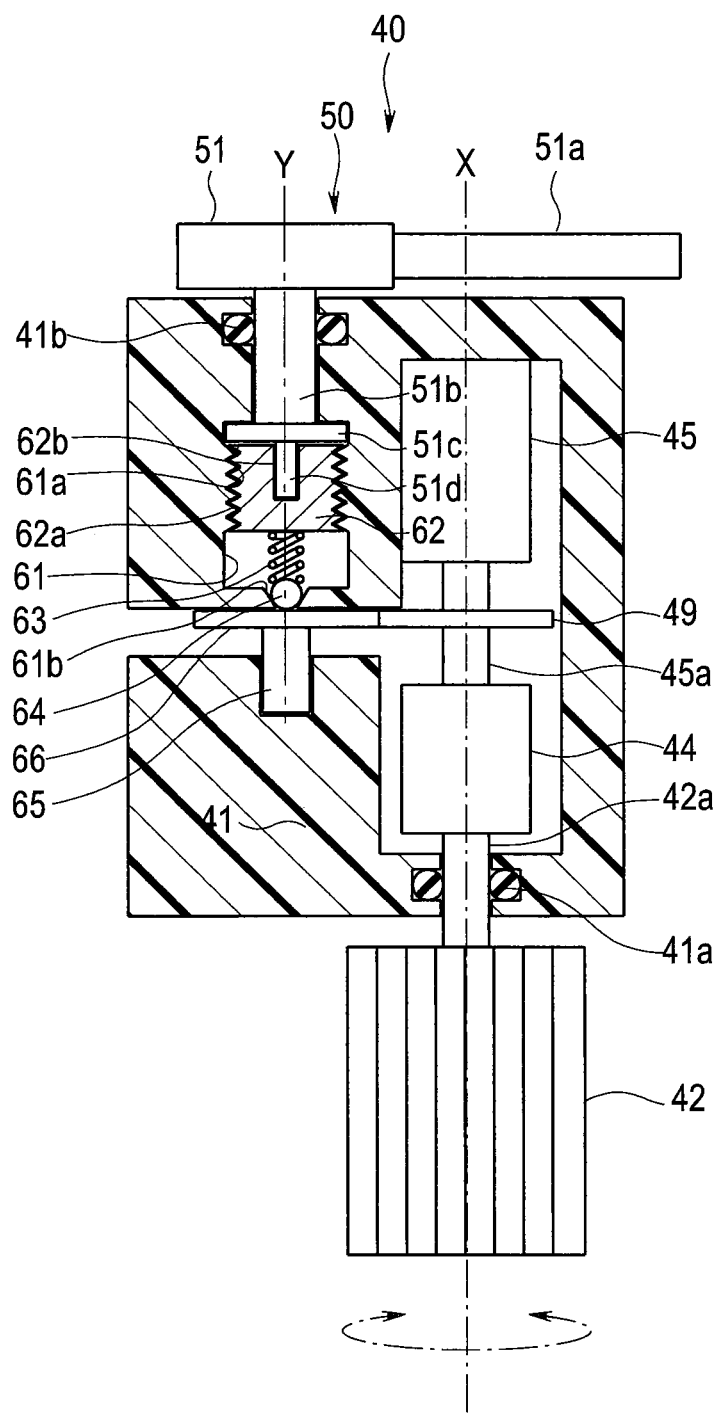
FIG. 22 is a cross-sectional view illustrating the configuration of an RL angular operation portion of a third modification of the third embodiment according to the present invention.
Figure 23:
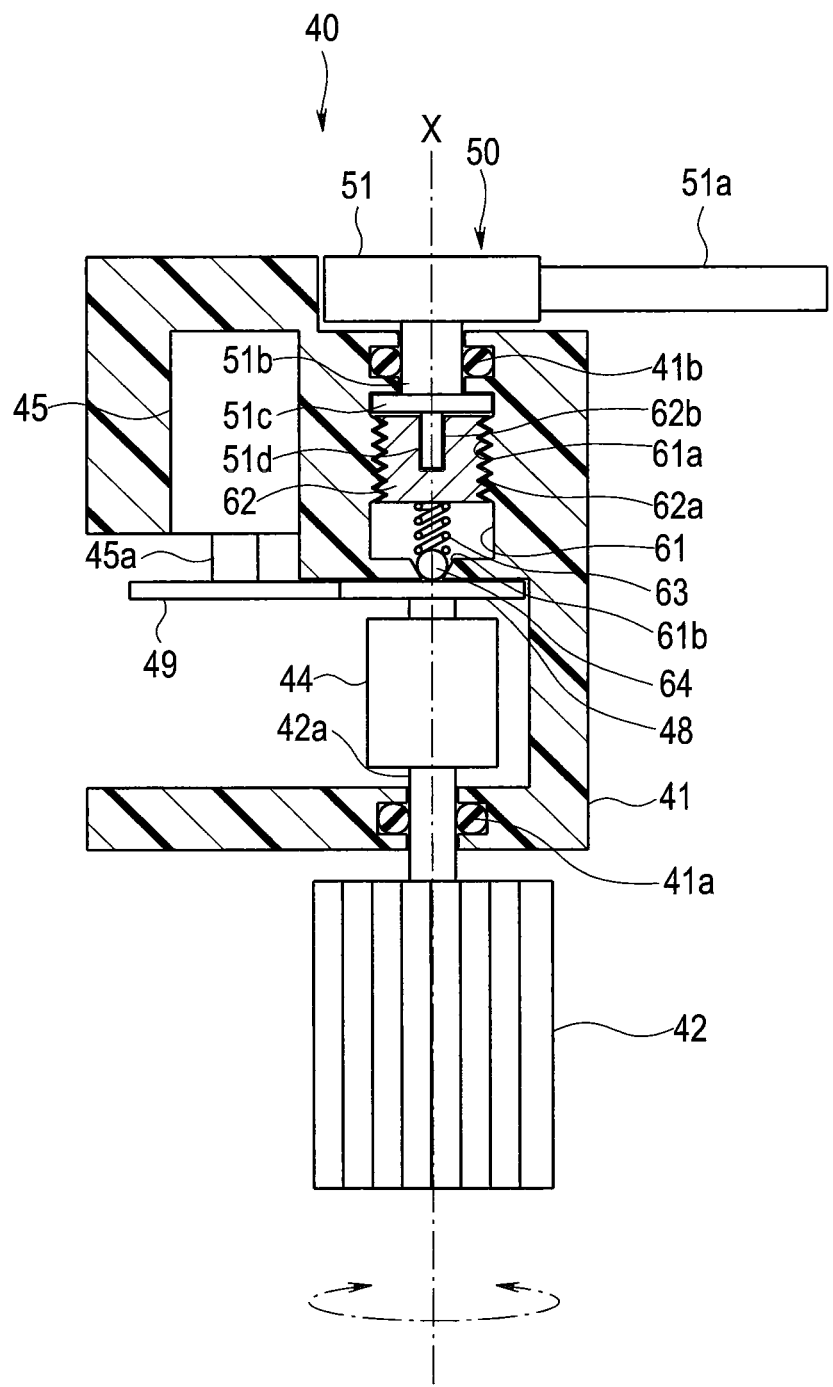
FIG. 23 is a cross-sectional view illustrating the configuration of an RL angular operation portion of a fourth modification of the third embodiment according to the present invention.

FIG. 18 to FIG. 23 relate to the third embodiment of the present invention. FIG. 18 is a cross-sectional view illustrating the configuration of an RL angular operation portion. FIG. 19 is a cross-sectional view for describing an action of the RL angular operation portion. FIG. 20 is a cross-sectional view illustrating the configuration of an RL angular operation portion according to a first modification. FIG. 21 is a cross-sectional view illustrating the configuration of an RL angular operation portion according to a second modification. FIG. 22 is a cross-sectional view illustrating the configuration of an RL angular operation portion according to a third modification. FIG. 23 is a cross-sectional view illustrating the configuration of an RL angular operation portion according to a fourth modification.

As shown in FIG. 18, the endoscope 2 of the present embodiment has a configuration in which a mechanism configured to restrain rotation of the sensor rotation shaft 45a of the potentiometer 45 that is provided in the engagement portion 50 of the RL angular operation portion 40 is different from the above-described first embodiment and second embodiment.

More specifically, the engagement portion 50 of the RL angular operation portion 40 has a substantially cylindrical threaded portion 62 that rotates together with the RL engagement lever 51 and with which a rectangular block-shaped engagement block 51d that is formed on the undersurface of the outward flange 51c that is formed on the lever rotation shaft 51b of the RL engagement lever 51 engages.

The threaded portion 62 is housed inside a hollow portion 61 that is formed in the case body 41. An external thread portion 62a is formed in the outer circumference of the threaded portion 62. The external thread portion 62a screws into an internal thread portion 61a that is formed in an inner circumferential wall forming the hollow portion 61. A slot 62b that is a concave portion with which the engagement block 51d engages is formed at an upper part of the threaded portion 62.

Note that when the threaded portion 62 is rotated, the threaded portion 62 moves so as to advance or retract along the rotation axis X direction.

The engagement portion 50 of the present embodiment further includes a coil spring 63 that is arranged so as to contact against the undersurface of the threaded portion 62 inside the hollow portion 61 of the case body 41, and a spherical body 64 that is pressed downward (toward the distal end side) by the coil spring 63.

Note that, in the case body 41, a spherical body receptacle 61b is formed that is a hole portion formed in a tapered shape so that a portion of the outer surface of the spherical body 64 is exposed and protrudes from a lower end portion forming the hollow portion 61. Note that the other components are the same as in the above described first embodiment.

In the engagement portion 50 of the RL angular operation portion 40 of the present embodiment configured as described above, when the lever body 51a of the RL engagement lever 51 is rotated in a predetermined direction, the threaded portion 62 also rotates and moves forward or rearward along the longitudinal direction of the RL angular operation portion 40 which is the vertical direction inside the hollow portion 61 in accordance with the amount of threading between the external thread portion 62a and the internal thread portion 61a.

As shown in FIG. 19, when the threaded portion 62 moves downward (toward the distal end side), the engagement portion 50 pushes down the coil spring 63, and the spherical body 64 presses the upper end surface of the sensor rotation shaft 45a of the potentiometer 45.

As a result, frictional resistance arises that is generated by the pressing force from the spherical body 64, and rotation of the sensor rotation shaft 45a in a reverting direction against the rotational force applied from the initial position reversion mechanism portion 44 is restrained.

Therefore, similarly to the first embodiment, the operator can fix the bending state in the RL direction of the bending portion 23a at a desired bending angle in, for example a range of 0° to ±180° in accordance with the rotation amount of the lever body 51a of the RL engagement lever 51. Note that the other actions are the same as in the respective embodiments described above.

With the above-described endoscope 2 of the present embodiment also, an operator can easily switch between a state in which the bending state of the bending portion 23a that is bent to a predetermined angle when the operator rotationally operates the RL operation dial 42 is fixed (maintained) even when the operator releases the hand from the RL operation dial 42, and a state in which the bending portion 23a returns as far as a position that is at a predetermined bending angle upon the operator releasing the hand from the RL operation dial 42.

That is, similarly to the first embodiment and second embodiment, the endoscope 2 of the present embodiment is also configured so that, by a rotational operation of the lever body 51a of the RL engagement lever 51, the operator can, at will, switch on or off a reversion function whereby the bending portion 23a returns as far as a position that is at a predetermined bending angle upon the operator releasing the hand from the RL operation dial 42.

Note that, in the endoscope 2 of the present embodiment also, by rotating the lever body 51a of the RL engagement lever 51 within an angle from the initial position (0° position shown in FIG. 5) to the predetermined angle θ, the operator can vary the frictional resistance that the sensor rotation shaft 45a receives from the spherical body 64.

Therefore, the operator can set so as to cause bending in the RL direction of the bending portion 23a to revert steplessly to an arbitrary angle in a range of, for example, 0° to ±180° in accordance with the rotational angle of the lever body 51a of the RL engagement lever 51 upon the operator releasing the finger that is operating the RL operation dial 42.

As described above, similarly to the first embodiment, the endoscope 2 of the present embodiment also has a configuration such that, by performing a rotational operation of the lever body 51a of the RL engagement lever 51, an operator can, at will, switch on or off a reversion function whereby the bending portion 23a returns as far as a position at a predetermined bending angle upon the operator releasing the hand from the RL operation dial 42.

That is, by rotationally operating the lever body 51a of the RL engagement lever 51 as far as a predetermined angle θ (see FIG. 5) in advance, the operator can rotationally operate the RL operation dial 42 and continuously fix (maintain) the bending state of the bending portion 23a that is bent at the predetermined angle even after the operator releases the hand from the RL operation dial 42, without the necessity of continuously pressing the RL operation dial 42 with a finger.

Further, by rotationally operating the lever body 51a of the RL engagement lever 51 as far as the initial position (0° position in FIG. 5) in advance, after rotationally operating the RL operation dial 42, the operator can cause the bending portion 23a to automatically revert to the initial position by releasing the hand from the RL operation dial 42.

In addition, by rotationally operating the lever body 51a of the RL engagement lever 51 to an arbitrary angle from 0° to θ in advance, after rotationally operating the RL operation dial 42, the operator can cause the bending portion 23a to automatically revert to a bending state at the arbitrary angle by releasing the hand from the RL operation dial 42.

MODIFICATIONS

The configurations of various modifications described hereunder may be adopted for the above-described endoscope 2, and in particular for the RL angular operation portion 40.

First Modification

As shown in FIG. 20, similarly to the second embodiment, the RL angular operation portion 40 may have a configuration in which the position of the engagement portion 50 is shifted away from the operation portion main body 24 in a direction that is orthogonal to the longitudinal direction (vertical direction) of the case body 41.

That is, the RL angular operation portion 40 has a rotation axis Y of the RL engagement lever 51 of the engagement portion 50 which is different to the rotation axis X of the RL operation dial 42, and which is located further away from the operation portion main body 24 than the rotation axis X. Note that the rotation axis X and the rotation axis Y are parallel axes.

The engagement portion 50 in this case has a gear shaft 65 that is provided in a condition in which the gear shaft 65 is rotatable around the rotation axis Y in the case body 41, and which is pressed by the spherical body 64.

A spur gear 66 is provided at the upper end of the gear shaft 65, and the gear 66 is meshed with the gear 49 of the sensor rotation shaft 45a. By this means, rotation and stopping of the gear shaft 65 and the sensor rotation shaft 45a are transmitted to each other.

In the engagement portion 50 of the RL angular operation portion 40 of the present modification configured as described above also, when the lever body 51a of the RL engagement lever 51 is rotated in a predetermined direction, the threaded portion 62 moves forward or rearward in the vertical direction along the longitudinal direction of the RL angular operation portion 40 inside the hollow portion 61.

Further, when the threaded portion 62 moves downward (toward the distal end side), the engagement portion 50 pushes down the coil spring 63, and the spherical body 64 presses the upper end surface of the gear shaft 65.

As a result, at the gear shaft 65 frictional resistance arises that is generated by the pressing force from the spherical body 64, and the sensor rotation shaft 45a is restrained through the gear 66 of the gear shaft 65, and rotation of the sensor rotation shaft 45a in a reverting direction against the rotational force applied from the initial position reversion mechanism portion 44 is restrained.

By configuring the RL angular operation portion 40 in this way, similarly to the second embodiment, in the RL angular operation portion 40, a distance between the RL operation dial 42 and the lever body 51a of the RL engagement lever 51 can be shortened. Therefore, it becomes easier for a forefinger or middle finger of the operator to reach both of the RL operation dial 42 and the RL engagement lever 51, and the accessibility when operating the components is improved.

In addition, the lever body 51a of the RL engagement lever 51 is provided at a position that is separated from the operation portion main body 24, and therefore the UD angle knob 26, the UD knob engagement lever 28, the switch 29, the suction button 30 and the air/water feeding button 31 do not become a hindrance, and furthermore the lever body 51a does not become a hindrance when operating the UD angle knob 26, the UD knob engagement lever 28, the switch 29, the suction button 30 and the air/water feeding button 31, and thus the operability of each of the components is also improved.

Second Modification

As shown in FIG. 21, in the RL angular operation portion 40, similarly to the first modification of the second embodiment, the RL engagement lever 51 of the engagement portion 50 may be provided on the lower side (distal end side) of the case body 41 in the vicinity of the RL operation dial 42, at a position that is away from the operation portion main body 24.

By this means, in the RL angular operation portion 40, by providing the RL engagement lever 51 of the engagement portion 50 on a lower side (distal end side) that is the distal end side of the endoscope 2, similarly to the RL operation dial 42, it becomes still easier for a forefinger or middle finger of the operator to reach the RL engagement lever 51, and thus the accessibility when operating the components can be improved.

Third Modification

As shown in FIG. 22, similarly to the second modification of the second embodiment, in the RL angular operation portion 40, a configuration may be adopted in which the rotation axis X of the RL operation dial 42 and the rotation axis Y of the RL engagement lever 51 of the engagement portion 50 are at different positions, the RL operation dial 42 may be provided at a position that is away from the operation portion main body 24, and the RL engagement lever 51 of the engagement portion 50 may be provided at a position that is close to the operation portion main body 24.

Fourth Modification

As shown in FIG. 23, similarly to the fourth modification of the second embodiment, in the RL angular operation portion 40, a configuration may be adopted in which the rotation axis X of the RL operation dial 42 and a rotation axis (X) of the RL engagement lever 51 of the engagement portion 50 are at the same position, the RL operation dial 42 and the RL engagement lever 51 may be provided at positions that are away from the operation portion main body 24, and the potentiometer 45 may be provided at a position that is closer to the operation portion main body 24 than the RL operation dial 42 and the RL engagement lever 51.

Fourth Embodiment

Next, a fourth embodiment of the present invention will be described with reference to the accompanying drawings. Note that components described in each of the foregoing embodiments are denoted by the same reference numerals, and a detailed description of the components is omitted hereunder.

Figure 24:
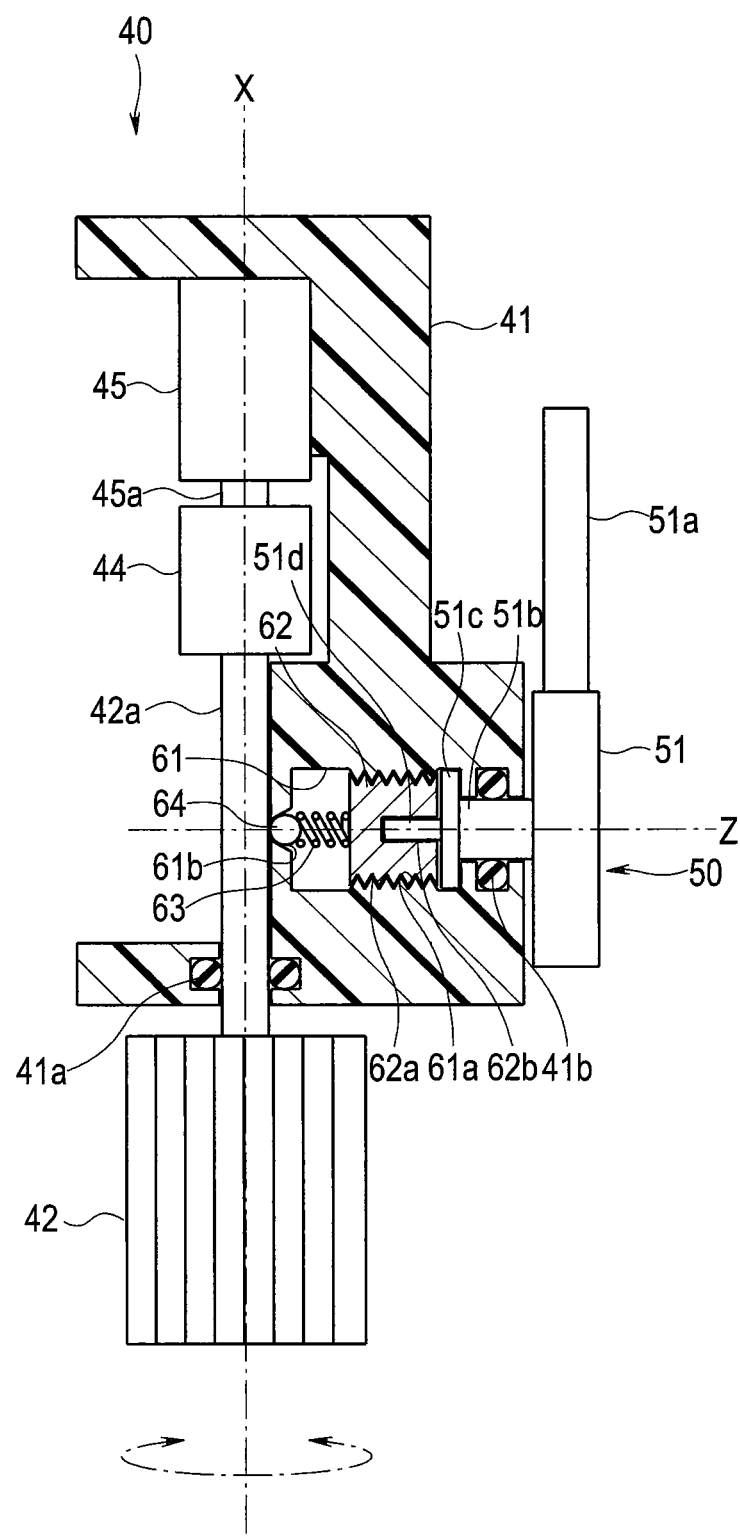
FIG. 24 is a cross-sectional view illustrating the configuration of an RL angular operation portion of a fourth embodiment according to the present invention.
Figure 25:
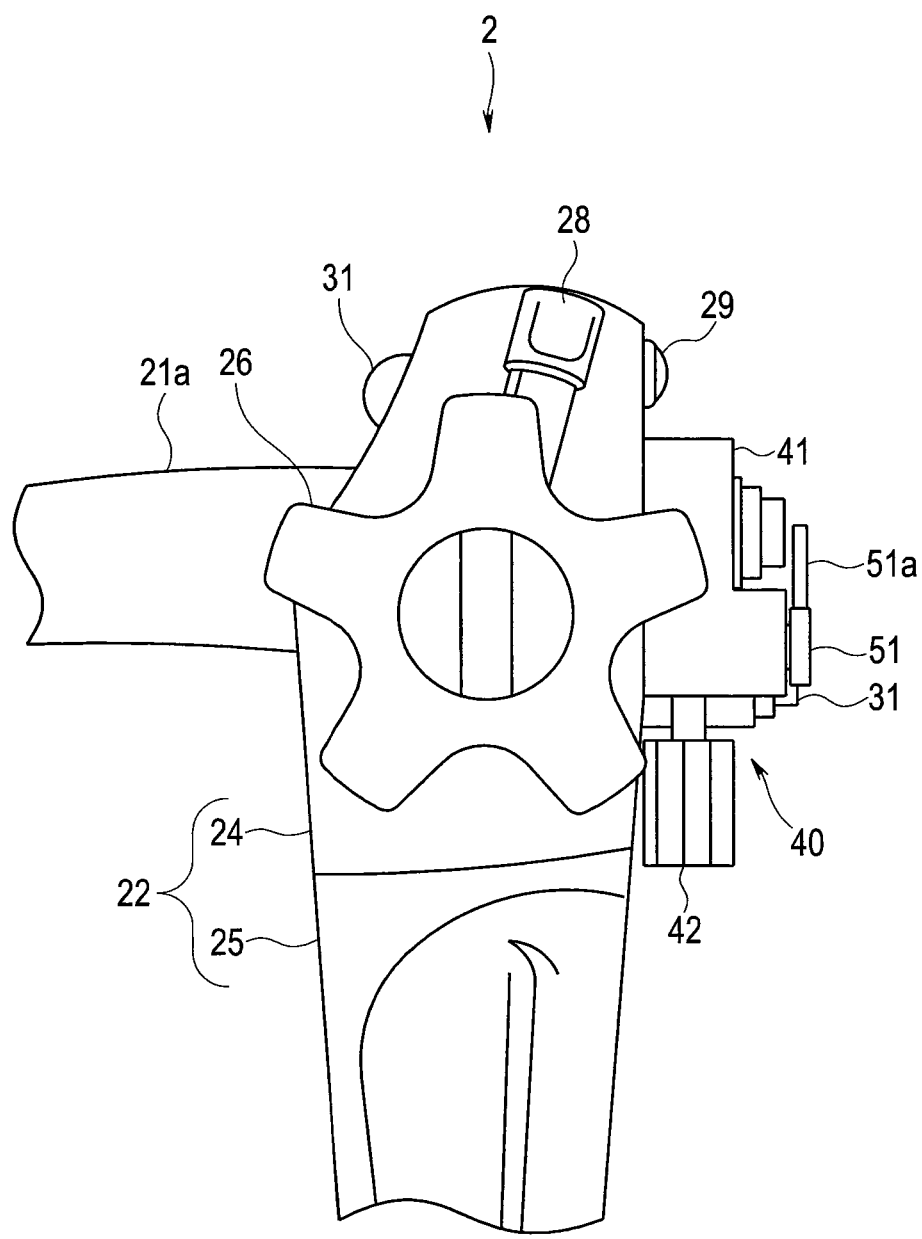
FIG. 25 is a side view illustrating the configuration of an operation portion of the fourth embodiment according to the present invention.
Figure 26:
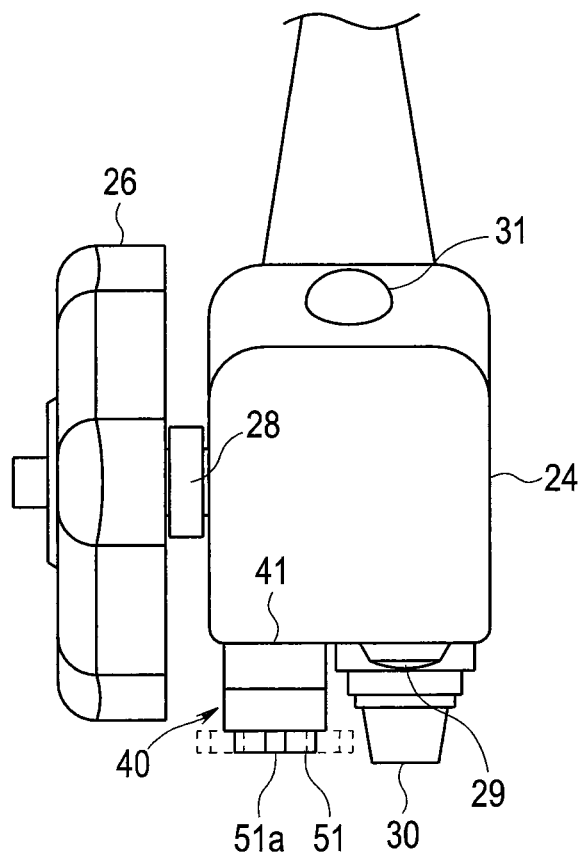
FIG. 26 is a top view of an operation portion in which an RL engagement lever is provided of the fourth embodiment according to the present invention.
Figure 27:
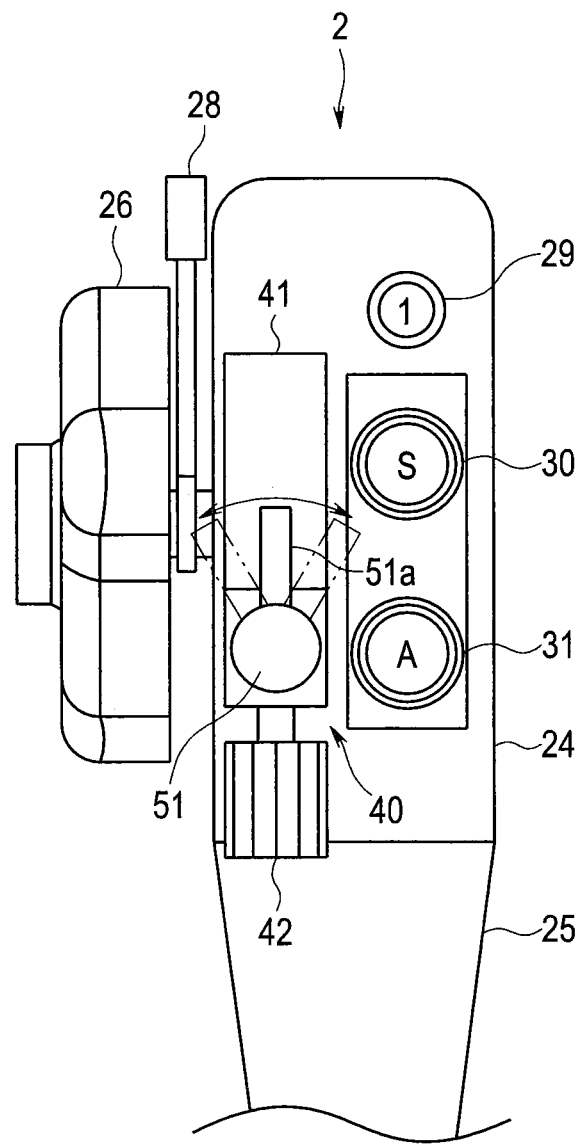
FIG. 27 is a front view of the operation portion in which the RL engagement lever is provided of the fourth embodiment according to the present invention.

FIG. 24 to FIG. 27 relate to the fourth embodiment of the present invention. FIG. 24 is a cross-sectional view illustrating the configuration of an RL angular operation portion of the fourth embodiment according to the present invention. FIG. 25 is a side view illustrating the configuration of an operation portion. FIG. 26 is a top view of an operation portion in which an RL engagement lever is provided. FIG. 27 is a front view of the operation portion in which the RL engagement lever is provided.

As shown in FIG. 24, the endoscope 2 of the present embodiment has a configuration in which the RL engagement lever 51 is provided on a side face that is orthogonal to the longitudinal direction (vertical direction) of the case body 41, at the position of the engagement portion 50 of the RL angular operation portion 40.

That is, the RL engagement lever 51 of the engagement portion 50 is provided so as to be rotatable about a rotation axis Z that is orthogonal to the rotation axis X of the RL operation dial 42.

Further, in the engagement portion 50 of the present embodiment, a mechanism that restrains rotation of the sensor rotation shaft 45a of the potentiometer 45 is, as a similar configuration as the third embodiment, a mechanism whereby the threaded portion 62 moves forward or rearward in accordance with rotation of the RL engagement lever 51.

Note that, in the engagement portion 50, when the threaded portion 62 moves towards the inside of the case body 41, the threaded portion 62 presses down the coil spring 63, and the spherical body 64 that is pressed by the coil spring 63 collides against a lateral circumferential face of the dial rotation shaft 42a of the RL operation dial 42 to thereby restrain rotation of the RL operation dial 42.

As a result, at the dial rotation shaft 42a, frictional resistance arises that is generated by the pressing force from the spherical body 64, and the sensor rotation shaft 45a is also restrained through the initial position reversion mechanism portion 44, and thus rotation of the sensor rotation shaft 45a in a reverting direction against the rotational force applied from the initial position reversion mechanism portion 44 is restrained. Note that the other components and actions are the same as in the above described embodiments.

With the above-described endoscope 2 of the present embodiment also, an operator can easily switch between a state in which the bending state of the bending portion 23a that is bent to a predetermined angle when the operator rotationally operates the RL operation dial 42 is fixed (maintained) even when the operator releases the hand from the RL operation dial 42, and a state in which the bending portion 23a returns as far as a position that is at a predetermined bending angle upon the operator releasing the hand from the RL operation dial 42.

That is, similarly to the first embodiment to third embodiment, the endoscope 2 of the present embodiment is also configured so that, by a rotational operation of the lever body 51a of the RL engagement lever 51, the operator can, at will, switch on or off a reversion function whereby the bending portion 23a returns as far as a position that is at a predetermined bending angle upon the operator releasing the hand from the RL operation dial 42.

Further, as shown in FIG. 25 to FIG. 27, in the RL angular operation portion 40 of the present embodiment, the RL engagement lever 51 of the engagement portion 50 is provided away from the operation portion main body 24, and the direction of a rotational operation of the lever body 51a of the RL engagement lever 51 is a direction that is orthogonal to the rotational operation direction of the RL operation dial 42.

Therefore, in the endoscope 2 of the present embodiment, because the operating direction of the RL operation dial provided on the RL angular operation portion 40 and the operating direction of the RL engagement lever 51 are different, operating errors can be prevented when performing an operation to bend the bending portion 23*a* and when performing an operation to fix/release the bending state of the bending portion 23*a*.

Note that although in the present embodiment a configuration is exemplified in which a mechanism that restrains rotation of the sensor rotation shaft 45*a* of the potentiometer 45 is a mechanism that restrains the dial rotation shaft 42*a* of the RL operation dial 42 by means of the spherical body 64 as a result of the threaded portion 62 pressing down the coil spring 63 when the RL engagement lever 51 is operated, the present embodiment is not limited to the configuration, and a cam mechanism described in the first embodiment and second embodiment may also be adopted.

Fifth Embodiment

Next, a fifth embodiment of the present invention will be described with reference to the drawings. Note that components described in each of the foregoing embodiments are denoted by the same reference numerals, and a detailed description of the components is omitted hereunder.

FIG. 28 to FIG. 33 relate to the fifth embodiment of the present invention.

Figure 28:
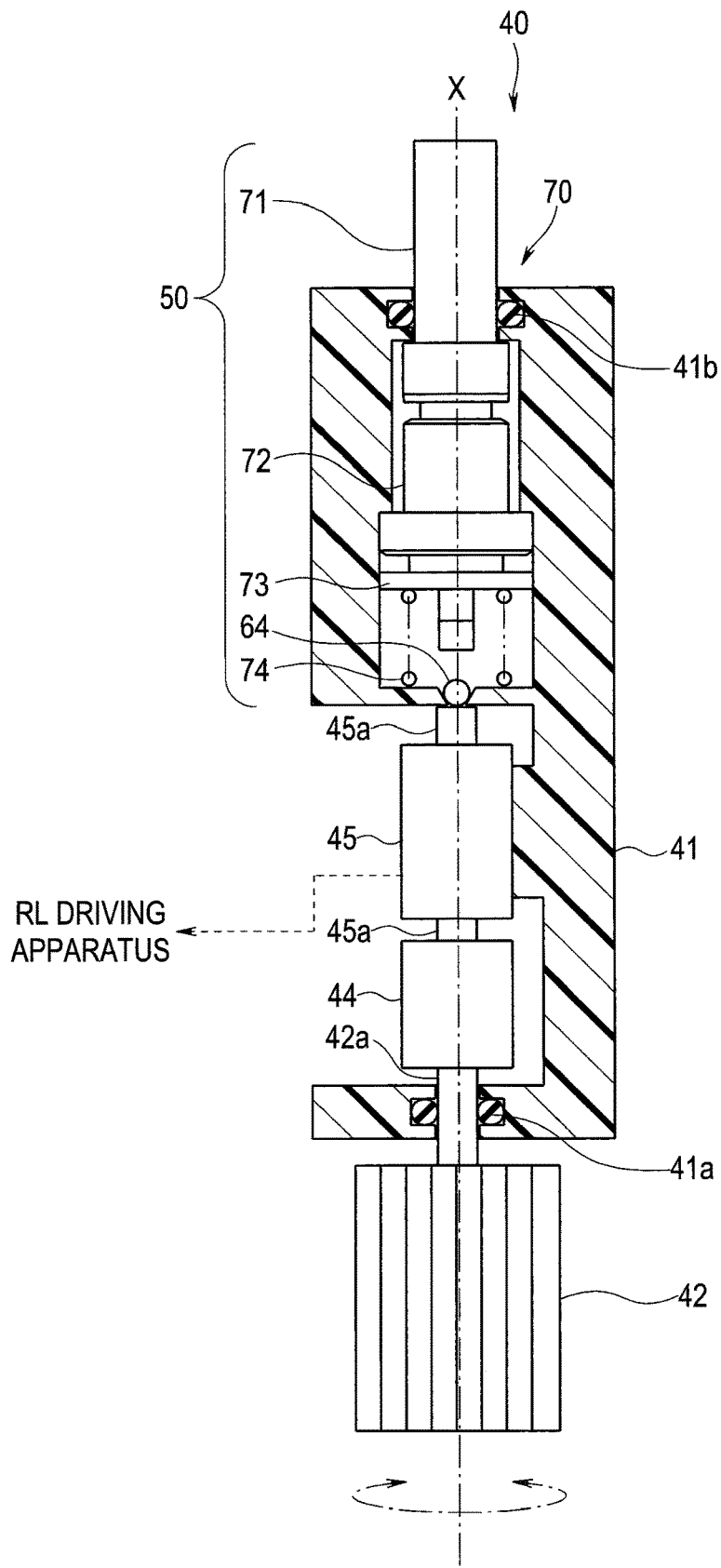
FIG. 28 is a cross-sectional view illustrating the configuration of an RL angular operation portion of a fifth embodiment according to the present invention.

As shown in FIG. 28, the endoscope 2 of the present embodiment has a configuration in which a mechanism configured to restrain rotation of the sensor rotation shaft 45*a* of the potentiometer 45 that is provided in the engagement portion 50 of the RL angular operation portion 40 is different from the above-described first embodiment and second embodiment, and in which a configuration that presses the spherical body 64 is different from the third embodiment.

More specifically, the engagement portion 50 of the RL angular operation portion 40 includes a switch portion 70 that is a so-called "knock-type feed switch mechanism portion", and has a configuration in which application of a pressing force to the spherical body 64 can be turned on or off by means of the switch portion 70.

Figure 29:
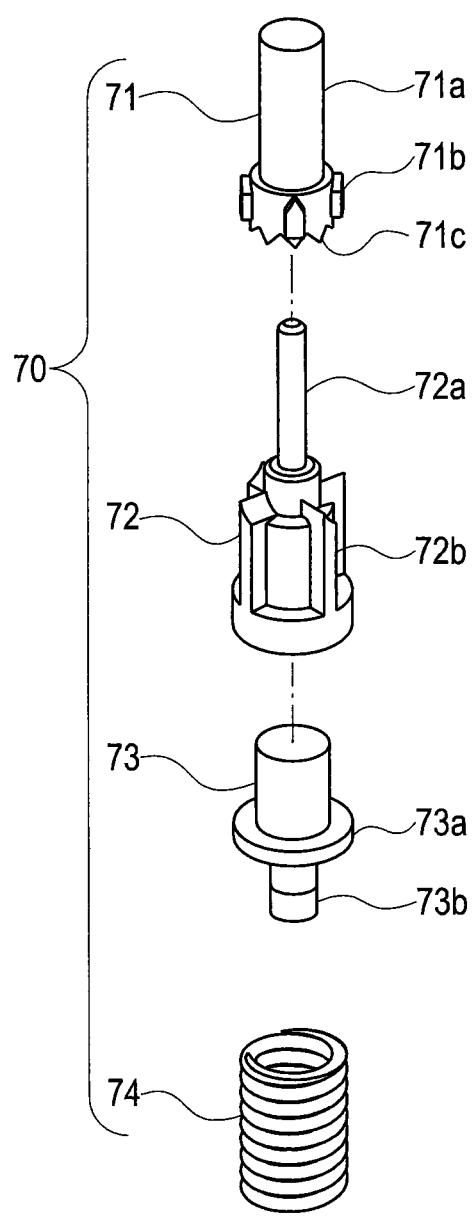
FIG. 29 is an exploded perspective view illustrating the configuration of a switch portion of the fifth embodiment according to the present invention.

The switch portion 70 is provided at an upper part of the case body 41, and as shown in FIG. 29 has a configuration that includes a knock rod 71, a rotor 72, a substantially columnar spring retainer 73 and a coil spring 74.

An opening portion is formed in a top surface portion of the case body 41 in which the switch portion 70 is housed, and an unshown groove is formed in an inner wall. The knock rod 71 is housed inside the case body 41 so that a rod-shaped operation rod body 71*a* protrudes from the opening portion, and is operated so as to project from and retract into the case body 41.

Note that an O-ring 41*b* is provided between the case body 41 and the knock rod 71, and the switch portion 70 is maintained in a watertight state even when the knock rod 71 is operated to project from or retract into the case body 41.

The knock rod 71 also includes, on an outer circumferential portion, a plurality of projection portions 71*b* that linearly move along grooves formed in the inner wall of the case body 41, and a concavo-convex portion 71*c* is formed on a face on the opposite side to the operation rod body 71*a*.

The rotor 72 includes a rod body 72*a* that is inserted into and rotated and held inside the knock rod 71, and a cam 72*b* for rotating upon contacting against the concavo-convex portion 71*c* in accordance with projection or recession of the knock rod 71 is formed on an outer circumferential portion.

That is, the rotor 72 is rotated about its own axis when the cam 72*b* contacts against the concavo-convex portion 71*c* of the knock rod 71.

An outward flange 73*a* is formed partway along an outer circumferential portion of the spring retainer 73. The outward flange 73*a* contacts against one end of the coil spring 74 and receives an urging force in one direction, which is the upward direction (toward the proximal end side) in this case.

A rubber block 73*b* that is a columnar elastic member that presses the spherical body 64 is arranged at a lower end portion of the spring retainer 73.

Figure 30:
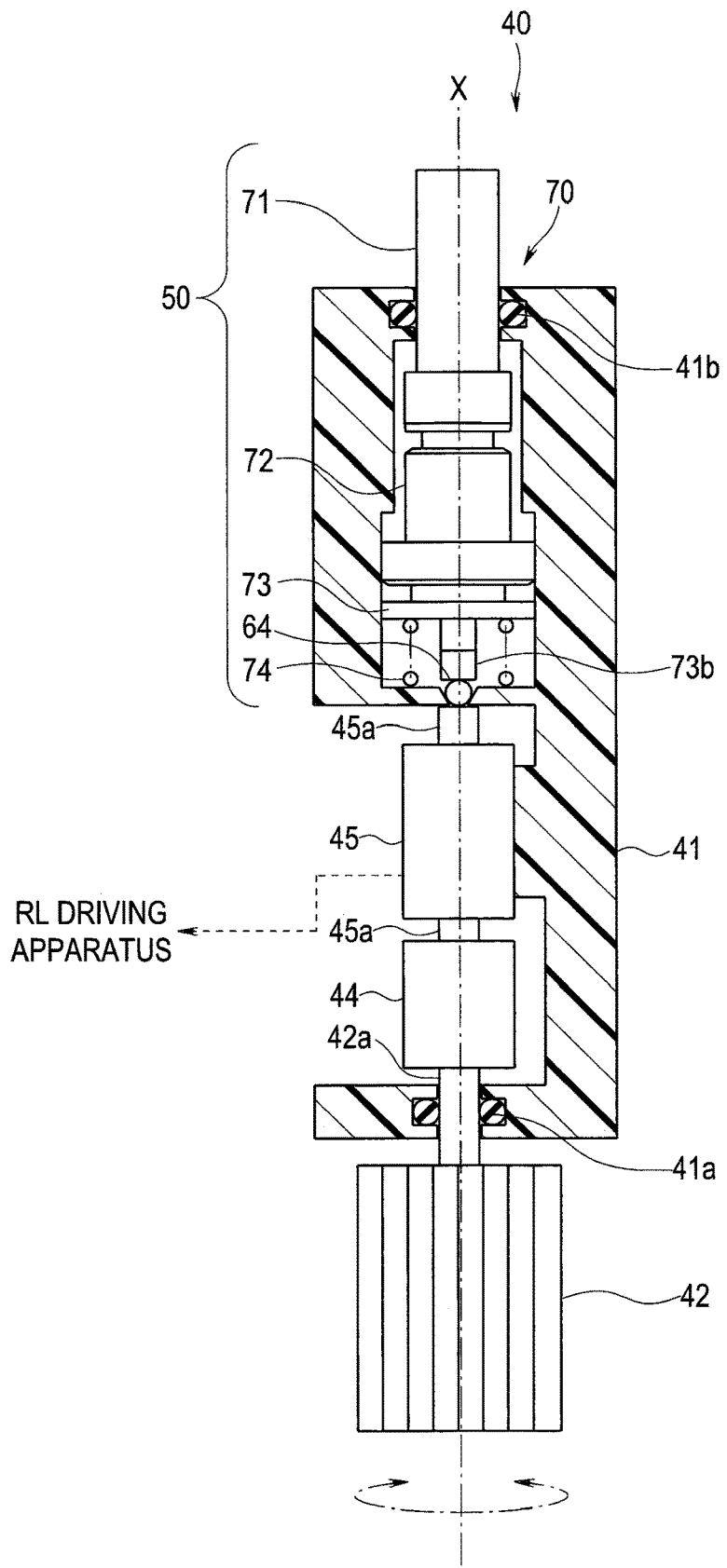
FIG. 30 is a cross-sectional view for describing an action of the RL angular operation portion of the fifth embodiment according to the present invention.

As shown in FIG. 30, in the switch portion 70 configured as described above, when the operation rod body 71*a* of the knock rod 71 is pressed by an operator, the rotor 72 rotates in a predetermined direction, and the cam 72*b* catches on a convex portion having an unshown V-shaped end surface that is formed on an inner face of the case body 41 in accordance with the rotation position.

At such time, the rotor 72 presses the spring retainer 73 and is restrained in a state in which the coil spring 74 is compressed thereby. As a result, in the switch portion 70, a state is entered in which a part of the operation rod body 71*a* of the knock rod 71 has retracted into the case body 41, and the rubber block 73*b* of the spring retainer 73 presses the spherical body 64 downward (toward the distal end side).

Thus, in the engagement portion 50, as a result of the rubber block 73*b* of the spring retainer 73 moving to the lower part (distal end side) of the case body 41, the spherical body 64 that is pressed downward (toward the distal end side) by the rubber block 73*b* collides against the lateral circumferential face of the dial rotation shaft 42*a* of the RL operation dial 42 to thereby restrain rotation of the RL operation dial 42.

As a result, at the dial rotation shaft 42*a*, frictional resistance arises that is generated by the pressing force from the spherical body 64, and the sensor rotation shaft 45*a* is also restrained through the initial position reversion mechanism portion 44, and thus rotation of the sensor rotation shaft 45*a* in a reverting direction against the rotational force applied from the initial position reversion mechanism portion 44 is restrained.

On the other hand, in the switch portion 70, if the operation rod body 71*a* of the knock rod 71 that has one part which has retracted into the case body 41 is pushed down once more by the operator, the rotor 72 rotates further in the predetermined direction and the cam 72*b* is released from the V-shaped end surface (unshown) that is formed in the convex portion of the case body 41.

At such time, the rotor 72 is returned by receiving the urging force of the coil spring 74 through the spring retainer 73, and the operation rod body 71*a* of the knock rod 71 enters a state in which the operation rod body 71*a* projects relative to an exterior portion 31.

As a result, the rubber block 73*b* of the spring retainer 73 moves upward (toward the proximal end side), and a pressing force on the spherical body 64 is released. The other components and actions are the same as in the respective embodiments described above.

In the above-described endoscope 2 of the present embodiment, by pushing down the knock rod 71 of the switch portion 70 that is provided in the engagement portion 50 of the RL angular operation portion 40, an operator can easily switch between a state in which the bending state of the bending portion 23*a* that is bent to a predetermined angle when the operator rotationally operates the RL operation dial 42 is fixed (maintained) even when the operator releases the hand from the RL operation dial 42, and a state in which the bending portion 23a returns as far as a midway position at which the bending portion 23a is in a substantially straight shape upon the operator releasing the hand from the RL operation dial 42.

That is, the endoscope 2 of the present embodiment has a configuration such that, by performing an operation to push down the knock rod 71 of the switch portion 70, an operator can, at will, switch on or off a reversion function whereby the bending portion 23a returns as far as a position that is at a predetermined bending angle when the operator releases the hand from the RL operation dial 42.

Further, the RL angular operation portion 40 of the present embodiment has a configuration in which the operation rod body 71a of the knock rod 71 of the switch portion 70 protrudes from a top surface portion of the case body 41, which is a configuration in which a bending state of the bending portion 23a is fixed/released by an operation that pushes the operation rod body 71a of the knock rod 71 downward from an upper side (proximal end side) to a lower side (distal end side).

Thus, the endoscope 2 has a configuration which allows an operator to easily perform an operation that fixes/releases a bending state of the bending portion 23a.

Figure 31:
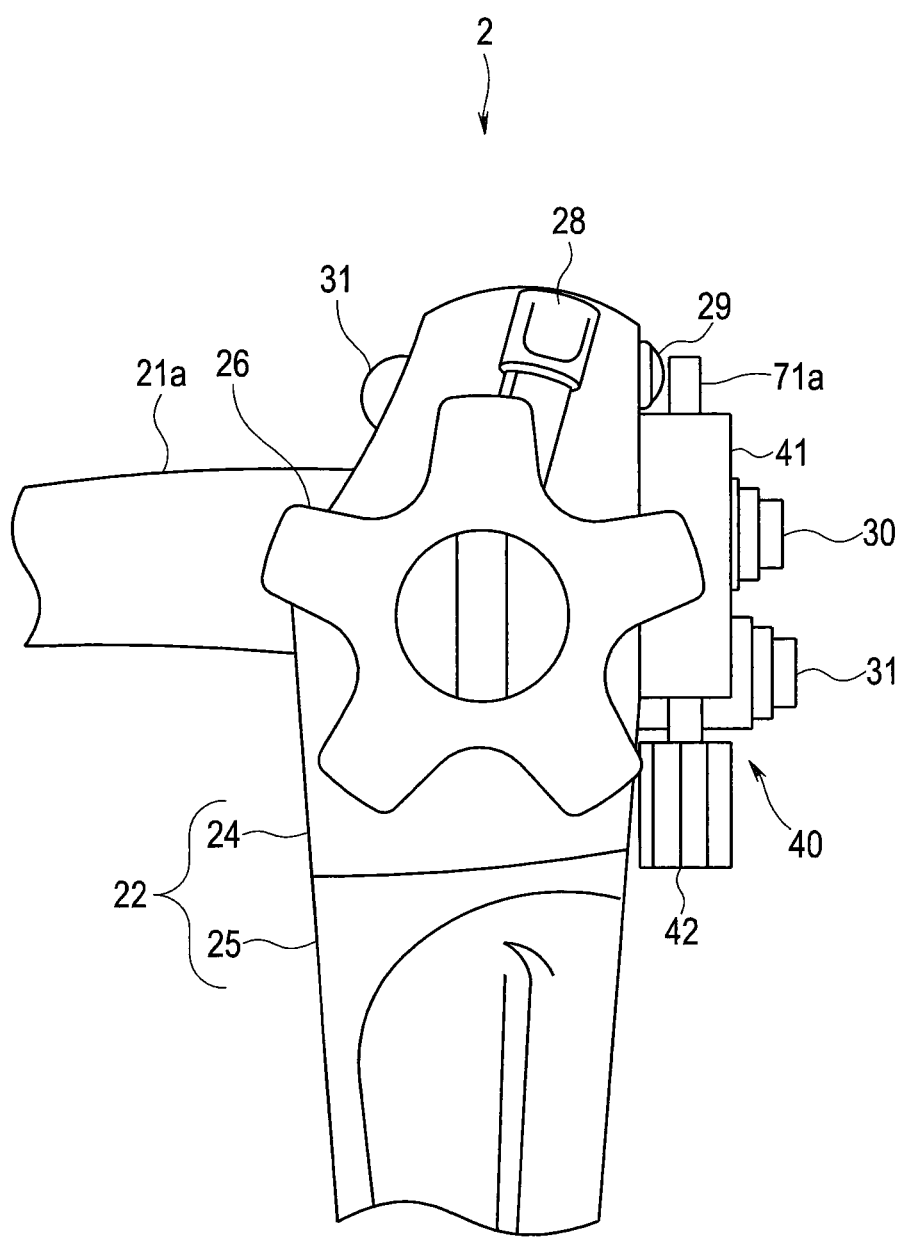
FIG. 31 is a side view illustrating the configuration of an operation portion of the fifth embodiment according to the present invention.
Figure 32:
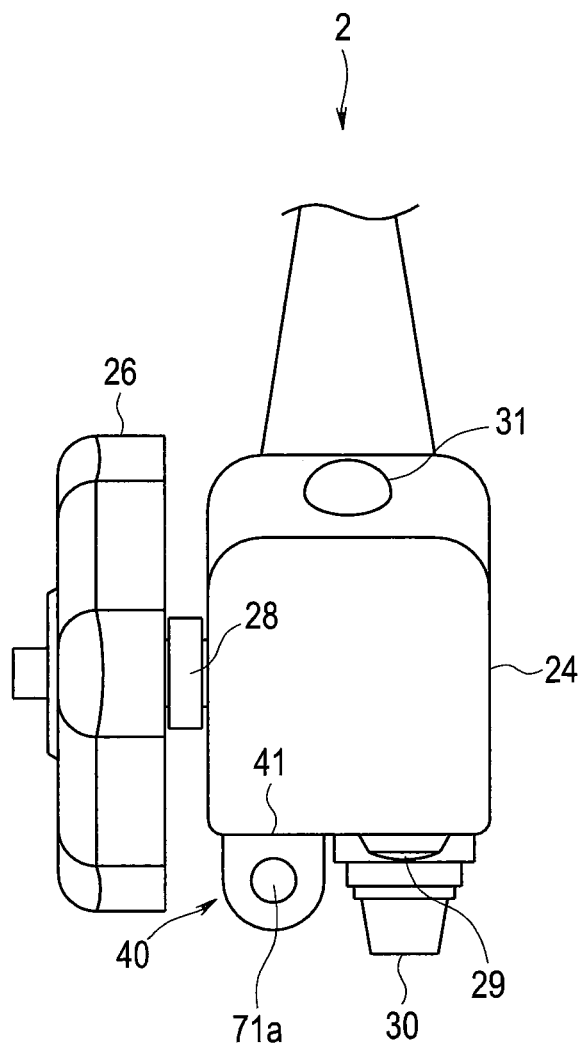
FIG. 32 is a top view of the operation portion in which an RL engagement lever is provided of the fifth embodiment according to the present invention.
Figure 33:
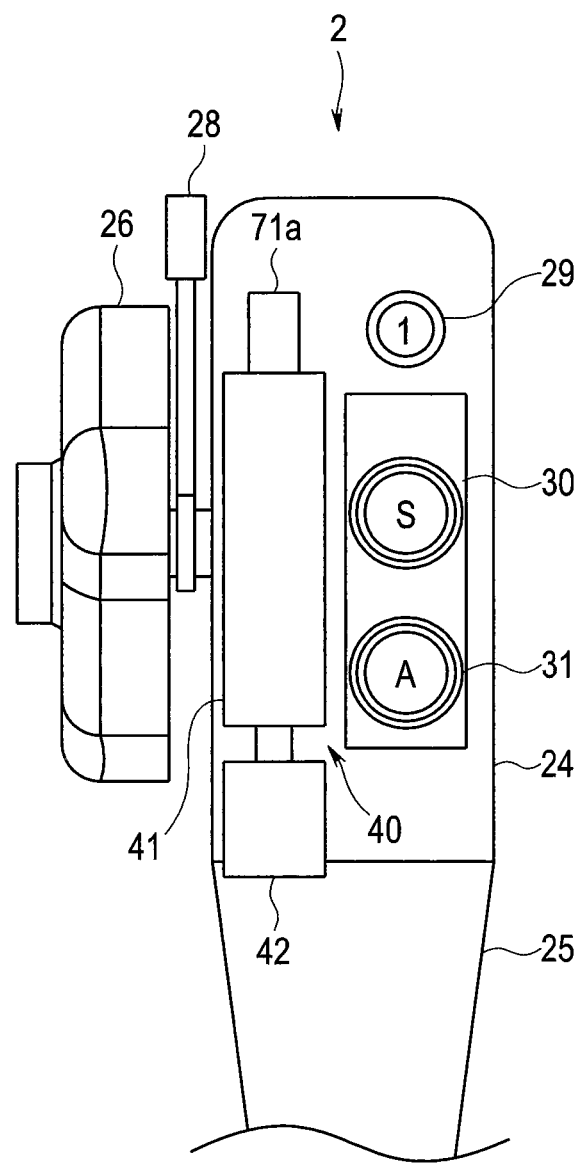
FIG. 33 is a front view of the operation portion in which the RL engagement lever is provided of the fifth embodiment according to the present invention.

In addition, as shown in FIG. 31 to FIG. 33, the endoscope 2 has a configuration in which the operation rod body 71a of the knock rod 71 of the switch portion 70 is provided at a position in which the operation rod body 71a projects from the top surface portion of the RL angular operation portion 40, and is operated by being pressed down at the position.

Thus, the operating range of the operation rod body 71a of the knock rod 71 is set so that not only does the operation rod body 71a not interfere with the UD angle knob 26, the UD knob engagement lever 28 and the switch 29, but also so that the operation rod body 71a of the knock rod 71 does not interfere with a finger of the operator when operating the UD angle knob 26 and the UD knob engagement lever 28.

By this means, when an operation of the knock rod 71 of the switch portion 70 is being performed, the UD angle knob 26, the UD knob engagement lever 28, the switch 29, the suction button 30 and the air/water feeding button 31 do not become a hindrance, and furthermore, when an operation of the UD angle knob 26, the UD knob engagement lever 28, the switch 29, the suction button 30 or the air/water feeding button 31 is being performed, the operation rod body 71a does not become a hindrance, and thus a decrease in the operability of each of the components is also prevented.

The invention described in the foregoing embodiments is not limited to the embodiments and modifications described above, and various modifications can be implemented within a range that does not deviate from the gist of the present invention in the implementing stage. Further, the above described embodiments include inventions of various stages, and various inventions can be extracted by appropriately combining a plurality of the disclosed configuration requirements.

For example, if a problem to be solved by the invention can be solved and the described effects of the invention are obtained even after omitting some of the configuration requirements from the entire configuration requirements shown in the embodiments, then the configuration obtained by omitting the configuration requirements can be extracted as an invention.

What is claimed is:

1. An endoscope operation mechanism arranged in an operation portion provided on a proximal end side of an insertion portion of an endoscope, the endoscope operation mechanism comprising:

a dial comprising a rotation shaft provided in a rotatable manner about a predetermined axis, the dial being configured to actuate a function of the endoscope upon being operated by an operator to rotate from an initial state;

an operation rod rotatably disposed on an axis parallel to the predetermined axis of the dial, the operation rod being rotationally operated by an operator; and a restraining portion configured to move in a longitudinal direction of the axis parallel to the predetermined axis by rotation of the operation rod, wherein the restraining portion switches between a first state that allows a change in position of the dial under an urging force, and a second state that suppresses a change in position of the dial by applying a resistance force to the urging force applied to the dial by moving forward or rearward, and wherein the restraining portion includes, a spring retainer including an elastic member at a distal end thereof and configured to move forward or rearward with the rotation of the operation rod, and a spherical body that is pressed by the elastic member with forward or rearward movement of the spring retainer.

2. The endoscope operation mechanism according to claim 1, further comprising a sensor configured to detect a change in position of the dial, and output an electrical signal that is in accordance with an amount of the change in position that is detected to a controller configured to control a driving source of a function of the endoscope.

3. The endoscope operation mechanism according to claim 1, wherein the dial actuates a function of the endoscope upon being rotated by an operator from an initial position.

4. The endoscope operation mechanism according to claim 3, further comprising a sensor that includes a rotation shaft configured to detect a rotation amount of the dial by rotating when a rotation of the rotation shaft of the dial is transmitted to the rotation shaft, and that is configured to output an electrical signal which is in accordance with the rotation amount that is detected to a control portion that is configured to perform driving control of a driving source of the function of the endoscope.

5. The endoscope operation mechanism according to claim 4, wherein the rotation shaft of the dial and the rotation shaft of the operation rod are disposed on a same axis.

6. The endoscope operation mechanism according to claim 5, wherein the dial is disposed at a position that is further to a distal end side than the sensor in a longitudinal direction of the endoscope, and the operation rod is disposed at a position that is further to a proximal end side than the sensor in a longitudinal direction of the endoscope.

7. The endoscope operation mechanism according to claim 5, wherein the operation rod is disposed along the rotation shaft, between the dial and the sensor.

8. The endoscope operation mechanism according to claim 4, wherein the rotation shaft of the dial and the rotation shaft of the operation rod are disposed on different axes.

9. The endoscope operation mechanism according to claim 8, wherein the dial is disposed at a position that is further to a distal end side than the sensor, and the operation rod is disposed at a position that is further to a proximal end side than the sensor.

10. The endoscope operation mechanism according to claim 8, wherein the operation rod is disposed between the dial and the sensor.

11. The endoscope operation mechanism according to claim 8, wherein the operation rod is arranged at a position that is further away from the endoscope operation portion than the dial.

12. The endoscope operation mechanism according to claim 11, wherein the operation rod is arranged in parallel with the dial.

13. The endoscope operation mechanism according to claim 1, wherein an operating range of the operation rod is set to a position such that the operation rod does not interfere with an operating range of a third operation member that operates another function of the endoscope which is different to the function of the endoscope that is provided in the operation portion.

14. An endoscope comprising the endoscope operation mechanism according to claim 1, in which a bending portion that is subjected to a bending operation by means of the endoscope operation mechanism is provided in the insertion portion.

15. The endoscope operation mechanism according to claim 1, wherein the operation rod includes,
a knock rod that is pushed down, and
a rotor configured to rotate by the knock rod being pushed down.

16. The endoscope operation mechanism according to claim 1, further comprising an initial state reversion mechanism configured to apply the urging force to the rotation shaft of the dial so as to return the dial to the initial state.

17. An endoscope operation mechanism arranged in an operation portion provided on a proximal end side of an insertion portion of an endoscope, the endoscope operation mechanism comprising:
a dial comprising a rotation shaft provided in a rotatable manner about a predetermined axis, the dial being configured to actuate a function of the endoscope upon being operated by an operator to rotate from an initial state;
an operation rod rotatably disposed on an axis parallel to the predetermined axis of the dial, the operation rod being rotationally operated by an operator; and
a restraining portion configured to move in a longitudinal direction of the axis parallel to the predetermined axis by rotation of the operation rod,
wherein the restraining portion switches between a first state that allows a change in position of the dial under an urging force, and a second state that suppresses a change in position of the dial by applying a resistance force to the urging force applied to the dial by moving forward or rearward, and
the restraining portion includes,
a threaded portion configured to rotate and move forward or rearward with the rotation of the operation rod,
a coil spring that is pressed by forward or rearward movement of the threaded portion, and
a spherical body that is pressed by an urging force of the coil spring.

\* \* \* \* \*